(12) United States Patent
Chen

(10) Patent No.: US 12,310,820 B1
(45) Date of Patent: May 27, 2025

(54) IMAGE PROCESSING METHOD AND OPERATION INTERFACE FOR EAR CLEANING ARRANGEMENT

(71) Applicant: Qinbin Chen, Shantou (CN)

(72) Inventor: Qinbin Chen, Shantou (CN)

( * ) Notice: Subject to any disclaimer, the term of this patent is extended or adjusted under 35 U.S.C. 154(b) by 0 days.

(21) Appl. No.: 18/759,978

(22) Filed: Jun. 30, 2024

(30) Foreign Application Priority Data

Apr. 29, 2024 (CN) .......................... 202410528323.1

(51) Int. Cl.
  *A61B 1/00* (2006.01)
  *A61B 1/227* (2006.01)
  *A61F 11/00* (2022.01)

(52) U.S. Cl.
  CPC ............ *A61F 11/006* (2013.01); *A61B 1/227* (2013.01)

(58) Field of Classification Search
  CPC ............................... A61F 11/006; A61B 1/227
  USPC ................................................. 600/178, 921
  See application file for complete search history.

(56) References Cited

U.S. PATENT DOCUMENTS

| | | | |
|---|---|---|---|
| 2019/0246873 A1* | 8/2019 | Lu ......................... | A61B 1/0623 |
| 2023/0290461 A1* | 9/2023 | Kong ..................... | G16H 30/40 |

OTHER PUBLICATIONS

Bebirdâ® R3 Ear Wax Removal Cleaner, 0.15 inch 1080P HD Ear Camera Lens with 6 LED Lights Intelligent Otoscope for iPhone, Android Phone(White) Amazon, 2021 (retrieved on Dec. 2, 2024) <URL: https://www.amazon.com/BEBIRDÂ®-Removal-0-15inch-Intelligent-Otoscope/dp/B097GN36GC> (Year: 2021).*

* cited by examiner

*Primary Examiner* — Timothy J Neal
*Assistant Examiner* — James Edward Boice
(74) *Attorney, Agent, or Firm* — Ying-Ting Chen

(57) ABSTRACT

An image processing method for a visual ear cleaning assembly, includes the following steps: a. activating a front camera of a smart terminal communicatively connected with the visual ear cleaning assembly; b. acquiring images from both a camera of the ear cleaning device and the front camera of the smart terminal; c. dividing the display area of the smarting terminal into two display areas, wherein one display area is defined as an ear canal display area, and the other display area is defined as an ear cleaning action display area; and d. displaying the image acquired form the camera of the ear cleaning device in the ear canal display area, and displaying the image acquired from the front camera of the smart terminal in the ear cleaning operation display area.

2 Claims, 18 Drawing Sheets

A

G1: acquiring a segment of video stream through the camera element 40, and selecting one frame image from the video stream as a selected image 412 through the processor 11. In another alternative embodiment, a frame image may also be captured as the selected image through the camera element 40 by the processor 11

G2: analyzing the attitude information at the time point corresponding to the selected image 412 through the processor 11 to obtain rotation angle change data and azimuth angle change data.

G3: determining whether the operating mode corresponding to the selected image 412 is the first operating mode or the second operating mode. If it is the first operating mode, executing step G4. If it is the second operating mode, executing step G5

G4: defining a preset angle β between a preset axis of the attitude sensor 70 and the horizontal direction, and determining whether |β-90| is less than or equal to a preset angle θ. If yes, executing step G5. If no, executing step G6.

G5: Adjusting the video stream captured by the camera element 40 based on the azimuth angle change data and displaying it in the image display area 62 through the processor 11

G6: Adjusting the video stream captured by the camera element 40 based on the rotation angle change data and displaying it in the image display area 62 through the processor 11

G7: Determining whether |β-90| is less than or equal to a preset horizontal switching angle. If yes, executing G8. If no, executing G9

G8: Adjusting the video stream captured by the camera element 40 based on the rotation angle change data and displaying it in the image display area 62 through the processor 11

G9: Adjusting the video stream captured by the camera element 40 based on the azimuth angle change data and displaying it in the image display area 62 through the processor 11

G10: Determining whether the angle between the preset axis of the attitude sensor 70 and the gravity direction is 0 degrees or within a preset range at the time point corresponding to the selected image 412 based on the azimuth angle change data. If yes, executing step G11. If no, executing step G12

G11: Adjusting the image captured by the camera element 40 based on the rotation angle change data and displaying it in the image display area 62 through the processor 11

G12: Adjusting the image captured by the camera element 40 based on the azimuth angle change data and displaying it in the image display area 62 through the processor 11

Fig.13

P1: identifying a target to be processed through acquiring a video stream captured by the camera element 40

P2: acquiring the attitude information at the time point corresponding to the selected image 412 to obtain recorded attitude information 111, wherein the recorded attitude information includes rotation angle change data and azimuth angle change data P3: during the process of the ear cleaning arrangement 100 moving toward the ear canal entrance, determining whether the ear canal entrance is still the target to be processed P4: Determining whether the ear cleaning arrangement 100 is shaking based on the attitude of the ear cleaning arrangement 100. If shaking occurs, adopting a corresponding image display method P41: acquiring a segment of video stream, and selecting one frame image as a selected image 412

P42: acquiring the current attitude information of the selected image 412 through the attitude sensor 70

P43: comparing the recorded attitude information with the current attitude information to determine whether the ear cleaning arrangement 100 has changed its moving direction P44: If the ear cleaning arrangement 100 has not changed its moving direction, acquiring another current video stream P45: comparing the acquired video stream with the other current video stream to obtain video stream change characteristics P46: generating a preset image 43 for a preset time based on the video stream change characteristics P47: displaying the preset image in the image display area 62

Fig.14

IMAGE PROCESSING METHOD AND OPERATION INTERFACE FOR EAR CLEANING ARRANGEMENT

CROSS REFERENCE OF RELATED APPLICATION

This application is a non-provisional application that claims priority under 35U.S.C. § 119 to China application number CN202410528323.1, filing date Apr. 29, 2024, wherein the entire content of which is expressly incorporated herein by reference.

BACKGROUND OF THE PRESENT INVENTION

Field of Invention

The present invention relates to a personal care field, and more particularly to a image processing method for the ear cleaning arrangement and operational user interface thereof.

Description of Related Arts

Ear canal care is a personal care procedure. The existing tool for ear canal care is an ear spoon. The ear spoon is a rod-shaped tool with a spoon-shaped end. The ear spoon is inserted into the ear canal. By contacting the ear spoon with the ear canal wall, earwax is removed from the ear canal wall, and then the ear spoon is taken out of the ear canal to remove the earwax from ear canal. During the process of removing earwax, the user is not aware of the exact location of the earwax. Instead, the user relies on the sensation of contact between the ear spoon and the ear canal wall to move the ear spoon out of the ear canal along the ear canal wall. Whether the ear pick has been cleaned is determined by observing if there is earwax on the ear spoon. Using this type of ear pick, ear canal care is essentially based on feeling.

To facilitate the observation of the position of earwax in the ear canal, a visual ear spoon has appeared on the market. The visual ear spoon uses a camera to capture images inside the ear canal, transmitting them to a smartphone. The images captured by the camera are displayed on the smartphone. The images captured by the camera are displayed on the smartphone, allowing the user to locate the earwax in the ear canal and the then remove the earwax with the ear spoon, causing the images captured by the camera to move as the visual ear spoon moves. This results in constantly changing images on the smartphone, making it difficult to accurately position the ear pick to remove the earwax, even when the location of the earwax is known. Additionally, the smartphone is placed in front of the user's eyes, while the user's ears are on either side of their head. When the user inserts the visual ear spoon into their ear canal, the images captured by the visual ear spoon are transmitted to the smartphone. The user views the images on the smartphone's display while cleaning their ear canal. However, this operation can be inconvenient, leading to instability and shaking when using the visual ear spoon.

Since the camera of the existing visual ear spoon is limited to a cylindrical mounting part, the images captured by the visual ear spoon is restricted to a circular shape. In contrast, the display screen of the smartphone is rectangular. The images captured by the visual ear spoon do not fill the entire display screen of the smartphone. In other words, the display screen of the smartphone may display additional content in areas on occupied by the image captured by the visual ear spoon. This additional content can potentially distract the user's attention. Given that the ear canal is a sensitive area of the human body, with the eardrum inside, such distraction may lead to injury to the user's ear canal. Therefore, it is necessary to incorporate attention-focusing settings on the operation interface.

SUMMARY OF THE PRESENT INVENTION

The invention is advantageous in that it provides an image processing method and an operation interface for an ear cleaning arrangement, wherein the image processing method of the ear cleaning arrangement provides a focusing operation user interface.

Another advantage of the invention is to provide an image processing method and an operation interface for an ear cleaning arrangement, wherein the image processing method of the ear cleaning arrangement provides an operation interface for observing the operation of the ear cleaning arrangement.

Another advantage of the invention is to provide an image processing method and operation interface for an ear cleaning arrangement, wherein the image processing method of the ear cleaning arrangement provides an operation user interface. The operation interface maintains a reference object at a certain position on the operation interface to facilitate operation.

Another advantage of the invention is to provide an image processing method and operation interface for an ear cleaning arrangement, wherein the operation interface maintains the display of a spoon element for facilitating operation.

Another advantage of the invention is to provide an image processing method and operation interface for an ear cleaning arrangement, wherein a target to be processed is determined by the direction of the spoon element.

Another advantage of the invention is to provide an image processing method and operation interface for an ear cleaning arrangement, wherein the image processing method of the ear cleaning arrangement provides an operation interface, and the operation interface includes a left ear display mode and a right ear display mode to respectively accommodate operations for the left ear and the right ear.

Another advantage of the invention is to provide an image processing method and operation interface for an ear cleaning arrangement, wherein the image processing method of the ear cleaning arrangement provides an automatic switching between the left ear display mode and the right ear display mode.

Another advantage of the invention is to provide an image processing method and operation interface for an ear cleaning arrangement, wherein the image processing method for the ear cleaning arrangement comprises an image stabilization processing method.

Another advantage of the invention is to provide an image processing method and operation interface for an ear cleaning arrangement, wherein the image processing method of the ear cleaning arrangement provides an image stabilization processing method for recognizing image features.

Additional advantages and features of the invention will become apparent from the description which follows, and may be realized by means of the instrumentalities and combinations particular point out in the appended claims.

According to the present invention, the foregoing and other objects and advantages are attained by an image processing method for a visual ear cleaning arrangement is executed on one or more processors for processing image information collected by a visual ear cleaning arrangement, wherein the visual ear cleaning arrangement comprises a cleaning assembly, a fixing assembly, a camera element, an attitude sensor, and a light source assembly, wherein the camera element and the light source assembly are installed in the fixing assembly, the cleaning assembly is configured to an end portion of the fixing assembly for at least a port of the cleaning assembly is within the image capture range of the camera element, the imagine processing method comprises the steps of:

A. activating a front camera of a smart terminal communicatively connected with the visual ear cleaning arrangement;

B. acquiring images from the camera element and the front camera of the smart terminal separately;

C. dividing a display screen of the smart terminal into two display areas, wherein one display area is defined as ear canal display area and the other display area is defined as operation display area, D. display the images acquired from the camera in the ear canal display area, and displaying the images acquired from the front camera of the smart terminal in the ear picking action display area.

According to an preferred embodiment of the present invention, further comprising:

E. automatically switching to the corresponding ear canal display mode by identifying the ear being cleaned by the visual ear cleaning arrangement, wherein if the left ear is being cleaned, the display mode is switched to the left ear display mode, and if the right ear is being cleaned, the display mode is switched to the right ear display mode.

In a preferred embodiment of the present application, the cleaning assembly is an ear spoon assembly, wherein the ear spoon assembly displayed in the right ear mode is defined as a standard display mode, and the ear spoon assembly displayed in the left ear mode is the mirror image of the ear spoon assembly displayed in the right ear mode.

In a preferred embodiment of the present application, step E further comprises the following steps:

E1. mirroring the image acquired from the front camera of the smart terminal to obtain a processed image;

E2. identifying which side of the user's head the visual ear cleaning arrangement is on; and E3. determining the ear of the user currently being cleaned by the visual ear cleaning arrangement, wherein if the left ear is being cleaned, it is determined to be the left ear mode, and if the right ear is being cleaned, it is defined as the right ear mode.

To achieve at least the above advantages and other advantages and in accordance with the purpose of the present application, as embodied and broadly described, there is provided an image processing method for an ear cleaning arrangement is executed on one or more processors for processing image information collected by an ear cleaning arrangement, wherein the ear cleaning arrangement includes a cleaning assembly, a fixing assembly, a camera element, an attitude sensor, and a light source assembly, wherein the camera and the light source assembly are mounted on the fixing assembly, and the cleaning assembly is disposed at one end of the fixing assembly so that at least part of the cleaning assembly is within the image capture range of the camera, wherein the method comprises the steps of:

S1. determining a video stream display area on an operation user interface, wherein the video stream display area is circular, and the video stream in the video stream display area is sourced from the camera element;

S2. defining the video stream display area of the as an operation background area, and setting the operation background area to be the same background color;

S3. acquiring the current display mode and processing the video stream collected by the camera according to the corresponding display mode to obtain a processed video stream; and S4. displaying the processed video stream in the video stream display area.

In a preferred embodiment of the present invention, the background color is black.

In a preferred embodiment of the present invention, step S3 further comprises the following steps:

S31. identifying the cleaning assembly and a video background in the video stream collected by the camera, separately;

S32. determining the current display mode, wherein if the current display mode is a horizontal mode, executing step S33, and if the current display mode is a dynamic mode, executing step S34;

S33. when the ear cleaning arrangement rotates around the central axis of the ear cleaning arrangement, fixing the video background, and the cleaning assembly rotates with the ear cleaning arrangement; and S34. when the ear cleaning arrangement rotates around the central axis of the ear cleaning arrangement, fixing the cleaning assembly at a position in the video stream display area, and the video background rotates with the ear cleaning arrangement.

In a preferred embodiment of the present invention, step S33 further comprises the following steps:

S331. separating the cleaning assembly and the video background to obtain a cleaning assembly layer and a video background layer;

S332. locking the video background layer so that the video background layer is fixed in the video stream display area;

S333. removing the cleaning assembly layer;

S334. removing the video background of the video stream collected by the camera to obtain the cleaning assembly layer of the video stream collected by the camera; and S335. displaying the locked video background layer and the cleaning assembly layer of the video stream collected by the camera in the video stream display area of the operation interface.

In a preferred embodiment of the present invention, step S34 further comprises the following steps:

S341. separating the cleaning assembly and the video background to obtain a cleaning assembly layer and a video background layer;

S342. locking the cleaning assembly layer so that the cleaning assembly layer is fixed at a position in the video stream display area;

S343. removing the video background layer;

S344. removing the cleaning assembly of the video stream collected by the camera to obtain the video background layer of the video stream collected by the camera; and S335. displaying the locked cleaning assembly layer and the video background layer of the video stream collected by the camera in the video stream display area of the operation interface, wherein the video background layer collected by the camera is placed under the locked cleaning assembly layer.

In a preferred embodiment of the present invention, the cleaning assembly is an ear spoon element.

In a preferred embodiment of the present invention, the cleaning assembly is a forceps.

To achieve at least the above advantages and other advantages and in accordance with the purpose of the present application, as embodied and broadly described, there is provided an image processing method for an ear cleaning arrangement is executed on one or more processors for processing image information collected by an ear cleaning arrangement, wherein the ear cleaning arrangement includes a cleaning assembly, a fixing assembly, a camera, an attitude sensor, and a light source assembly, wherein the camera and the light source assembly are mounted on the fixing assembly, and the cleaning assembly is disposed at one end of the fixing assembly so that at least part of the cleaning assembly is within the image capture range of the camera, wherein the method comprises the steps of:

T1. acquiring a video stream of the inside of a user's ear canal;

T2. analyzing the acquired video stream to determine whether there is earwax in the ear canal video stream, and if there is earwax, continuing to analyze the acquired video stream to obtain the direction of the ear spoon assembly. Defining the earwax pointed to by the ear spoon assembly as the target to be cleaned. Recording the current attitude information of the ear cleaning arrangement and the current video stream information;

T3. monitoring the movement trajectory and direction of the ear cleaning arrangement by acquiring the attitude information provided by the attitude sensor of the ear cleaning arrangement and the video stream information provided by the camera, respectively;

T4. determining a new target to be cleaned based on the direction of the ear spoon assembly.

To achieve at least the above advantages and other advantages and in accordance with the purpose of the present application, as embodied and broadly described, there is provided an image processing method for an ear cleaning arrangement is executed on one or more processors for processing image information collected by an ear cleaning arrangement, wherein the ear cleaning arrangement comprises a cleaning assembly, a fixing assembly, a camera element, an attitude sensor, and a light source assembly, wherein the camera and the light source assembly are mounted on the fixing assembly, and the cleaning assembly is disposed at one end of the fixing assembly so that at least part of the cleaning assembly is within the image capture range of the camera, wherein the method comprises the steps of:

P1. selecting a frame from the video stream collected by the camera to be recorded as a recorded image and recognizing a target to be processed by analyzing the recorded image;

P2. acquiring attitude information corresponding to the time point of the recorded image to obtain recorded attitude information;

P3. during the process of the ear cleaning arrangement moving towards the target to be processed, determining whether the target to be processed has changed, wherein if the target to be processed has not changed, executing step P4, and if the target to be processed has changed, executing step P1;

P4. recognizing the attitude of the ear cleaning arrangement and determining whether the ear cleaning arrangement is shaking, and if shaking occurs, adopting a corresponding image display method.

In an embodiment of the present invention, step P1 further comprises the following steps:

P11. acquiring the video stream collected by the camera;

P12. selecting a frame from the acquired video stream as a selected image;

P13. defining the target pointed to by the ear spoon assembly in the selected image as the target to be processed, wherein if the target to be processed is an ear canal or earwax, executing step P14, and if the target to be processed is not the ear canal or earwax, executing step P11;

P14. confirming the target to be processed and defining the selected image as the recorded image.

In an embodiment of the present invention, step P4 further comprises the following steps:

P41. acquiring a segment of the current video stream and selecting a frame as the current selected image;

P42. acquiring current attitude information of the current selected image through the attitude sensor;

P43. comparing the recorded attitude information with the current attitude information to determine whether the ear cleaning arrangement has changed its moving direction, and if not, executing step P44;

P44. acquiring another current video stream for comparison with the current video stream to obtain video stream variation characteristics;

P45. generating a preset image for a preset time based on the video stream variation characteristics; and P46. displaying the preset image.

In an embodiment of the present invention, step P4 further comprises the following steps:

P4A. acquiring a segment of the current video stream and selecting a frame as the current selected image, recording the current selected image as a recorded image, and recording the attitude information of the current selected image as recorded attitude information;

P4B. acquiring the current attitude information of the current selected image through the attitude sensor and recording the current attitude information;

P4C. comparing the recorded attitude information with the current attitude information to determine whether the ear cleaning arrangement has changed its moving direction, and if not, displaying the recorded image.

In an embodiment of the present invention, step P4 further comprises the following steps:

P4a. acquiring a segment of the current video stream and selecting a frame as the current selected image;

P4b. analyzing the attitude information corresponding to the time point of the current selected image to obtain rotation variation data and orientation variation data;

P4c. determining whether the selected image corresponds to a first operation mode or a second operation mode, wherein if the first operation mode, executing step P4d, and if the second operation mode, executing step P4e, wherein the first operation mode is defined as moving from a horizontal direction to a vertical direction, and the second operation mode is defined as moving from a vertical direction to a horizontal direction;

P4d. defining the angle between a preset axis of the attitude sensor and the horizontal direction as $\beta$, and determining whether $|\beta-90|$ is less than or equal to a preset angle $\theta$, wherein if yes, executing step P4e, and if not, executing step P4f;

P4e. adjusting the video stream collected by the camera based on the orientation variation data and displaying;

P4f. adjusting the video stream collected by the camera based on the rotation variation data and displaying on the image display.

In an embodiment of the present invention, the cleaning assembly is an ear spoon element.

In an embodiment of the present invention, the cleaning assembly is a forceps.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 13 is a flowchart of an image processing method of the ear cleaning arrangement according to a preferred embodiment of the present application.

FIG. 14 is a flowchart of an image processing method of the ear cleaning arrangement according to a preferred embodiment of the present application.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
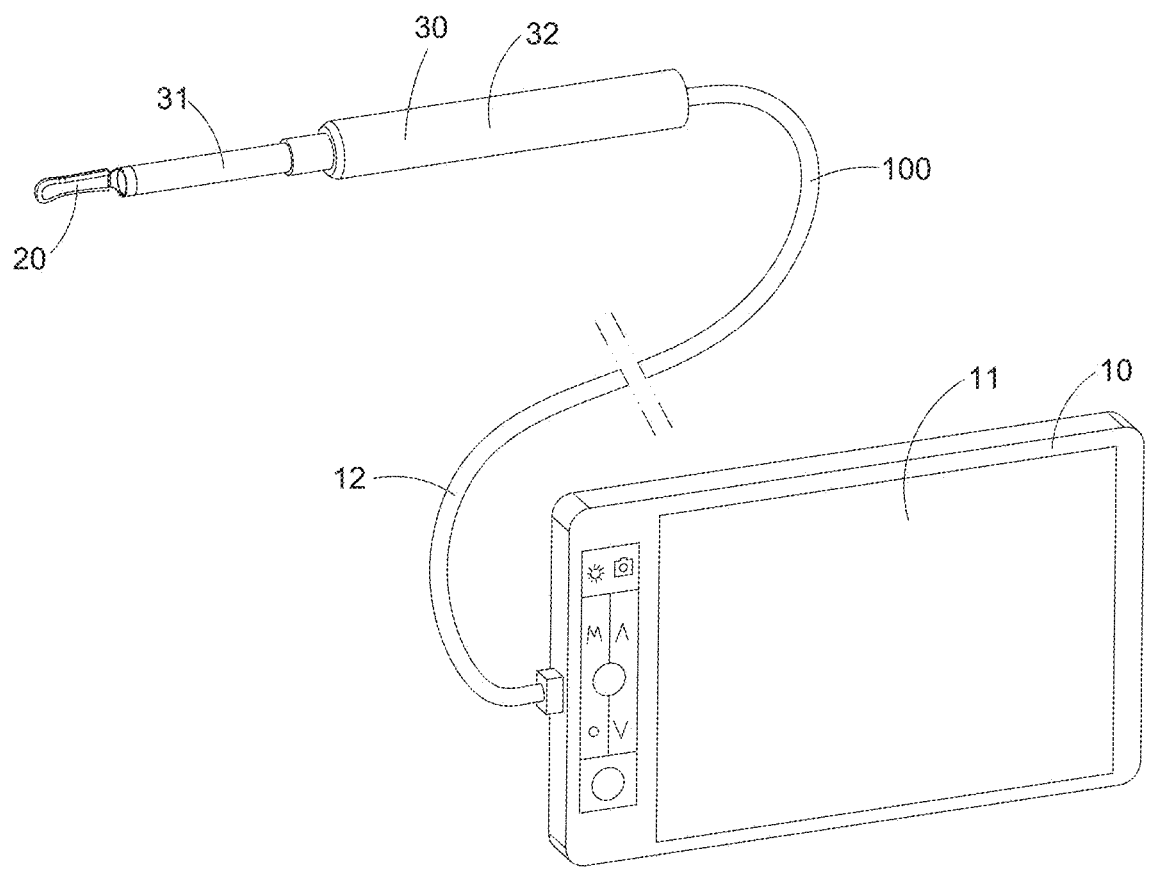
FIG. 1 is a perspective view of an ear cleaning arrangement according to a first preferred embodiment of the present invention.
Figure 2A:
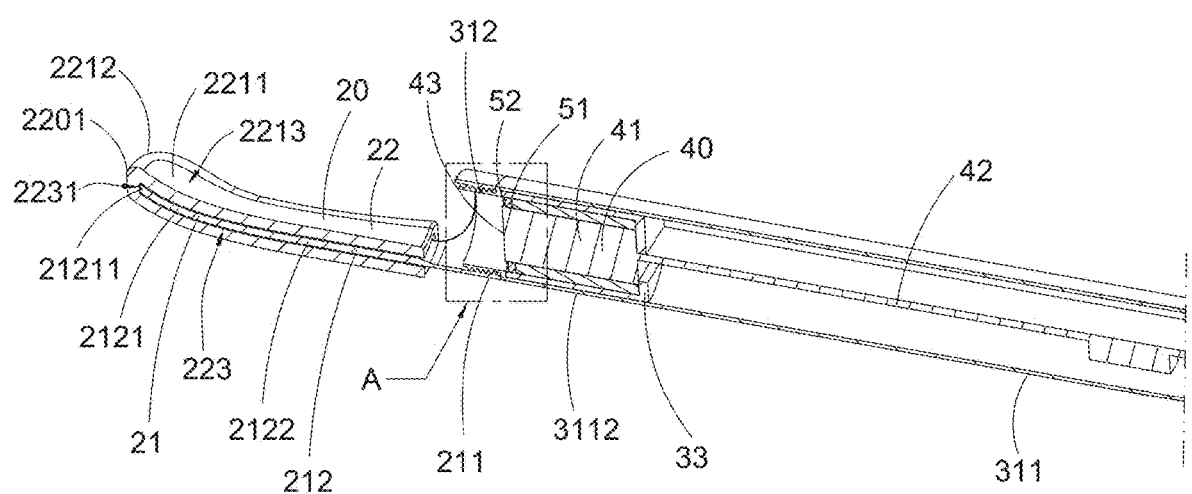
FIG. 2A is a sectional view illustrating an ear spoon assembly and a fixing rod of the ear cleaning arrangement according to the above first preferred embodiment of the present invention.
Figure 2B:
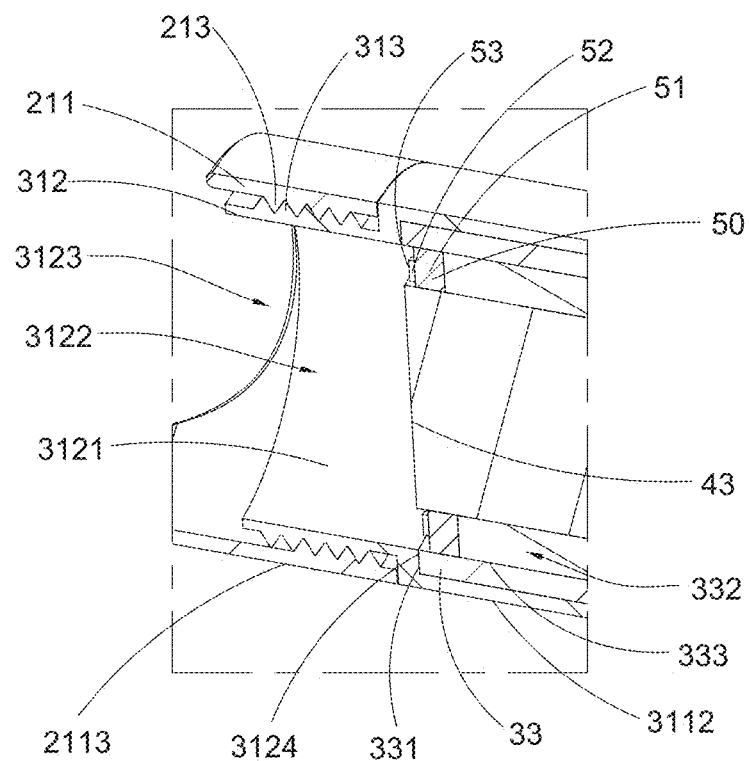
FIG. 2B is a partial enlarged view illustrating the ear spoon assembly and the fixing rod of the ear cleaning arrangement according to the above first preferred embodiment of the present invention.
Figure 2C:
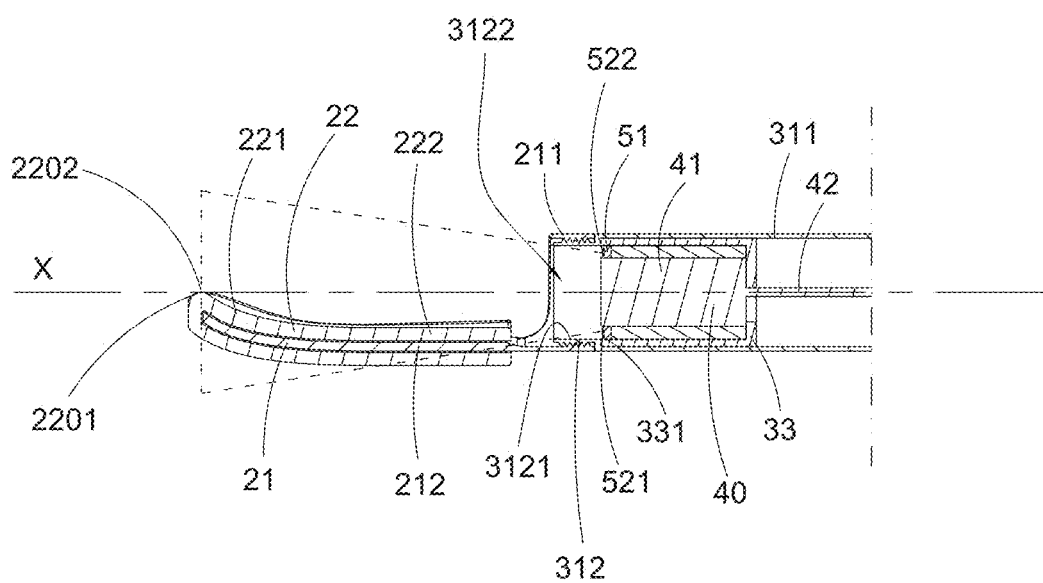
FIG. 2C is a sectional view illustrating the ear spoon assembly and a light guide barrel being in an assembled state according to the above first preferred embodiment of the present invention.

As shown in FIGS. 1 to 2C, the ear cleaning arrangement 100 according to a first preferred embodiment of the present invention is provided for use by a user to clean their own ears or the ears of others, such as children or the elderly. In this embodiment, the ear cleaning arrangement 100 is exemplified for use by the user to clean their own ears.

The ear cleaning arrangement 100 comprises an ear spoon assembly 20, a fixing assembly 30, a camera element 40, and a light source assembly 50. The camera element 40 and the light source assembly 50 are assembled within the fixing assembly 30. The camera element 40 is communicatively connected to a smart terminal 10, allowing images captured by the camera element 40 inside the ear to be displayed on the display screen of the smart terminal 10, enabling the user to observe the condition inside their ear and locate earwax. The ear spoon assembly 20 is connected to the fixing assembly 30 for cleaning earwax inside the ear. The camera element 40 and the light source assembly 50 are assembled within the fixing assembly 30, with the light source assembly 50 providing supplementary lighting for the camera element 40 to illuminate areas inside the ear, such as the concha and ear canal, during the ear cleaning process.

The fixing assembly 30 includes a fixing rod 31 and a handle 32. The fixing rod 31 is used to assemble the camera element 40 and the light source assembly 50, and the ear spoon assembly 20 is connected to the fixing rod 31. The handle 32 is connected to the fixing rod 31, allowing the user to grip it, thereby enabling the user to position the front end of the ear spoon assembly 20 inside their ear for cleaning.

In this embodiment of the present invention, the fixing rod 31 is embodied as a hollow fixing cylinder, with the camera element 40 and the light source assembly 50 being housed within the fixing cylinder. The diameter of the fixing rod 31 is smaller than that of the handle 32, with the handle 32 having a relatively larger diameter to facilitate the user's grip and operation. The fixing rod 31 and the handle 32 may be made of the same material and integrally extend from the handle 32, or the fixing rod 31 and the handle 32 may be assembled and fixed together by bonding or with elements such as screws.

In this embodiment, the ear spoon assembly 20 is detachably connected to the fixing rod 31 of the fixing assembly 30, allowing the user to replace the ear spoon assembly 20 with different sizes, thereby enabling the user to select a suitable ear spoon assembly 20 that fits their needs. In other words, the present invention can provide ear pick assemblies 20 of various sizes and styles for the user to choose and assemble onto the fixing rod 31. After detaching from the fixing rod 31 of the fixing assembly 30, the ear spoon assembly 20 can also be cleaned separately, thereby preventing water from entering the fixing assembly 30 and causing damage to the camera element 40 and the light source assembly 50.

The ear spoon assembly 20 in this embodiment is detachably connected to the fixing rod 31 of the fixing assembly 30, making it convenient for the user to replace the ear spoon assembly 20 of different sizes, so that the user can choose the suitable ear spoon assembly 20 for himself or herself. In other words, the present invention can provide ear spoon assemblies 20 of different sizes and styles for the user to choose and assemble on the fixing rod 31. After the ear spoon assembly 20 is detached from the fixing rod 31 of the fixing assembly 30, it can also be washed separately to avoid water entering the fixing assembly 30 and causing damage to the camera element 40 and the light source 50.

As shown in FIGS. 2A to 2C, the ear spoon assembly 20 comprises a rigid inner spoon 21 and a flexible outer spoon 22, and the flexible outer spoon 22 is detachably fitted on the rigid inner spoon 21. It can be understood that the rigid inner spoon 21 is made of rigid material such as metal, metal alloy, ceramic, plastic or wood. The flexible outer spoon 22 is made of flexible materials such as silicone, thermoplastic polyurethane elastomer rubber (TPU), Acrylonitrile-butadiene-styrene (ABS), polypropylene, polyimide, polyether ketone, polyvinyl chloride (PVC), ethylene-vinyl acetate copolymer (EVA), ethylene and alpha-olefin elastomer copolymer (POE), thermoplastic elastomer rubber (TPES) and other flexible plastics, which flexibly contact with the user's ear, thus will not scratch the user's ear.

The rigid inner spoon 21 comprises an installation part 211 and an inner spoon body 212, wherein the inner spoon body 212 is integrally extended from the installation part 211, and the flexible outer spoon 22 is sleeved on the inner spoon body 212. In this embodiment, the installation part 211 is in a barrel shape, and the inner spoon body 212 is integrally extended from a partial edge of the tubular installation part 211. The installation part 211 is used for being detachably assembled with the fixing rod 31.

As shown in FIGS. 2A to 2C, the installation part 211 is sleeved on an outer surface of the fixing rod 31, so that the inner wall of the front end of the fixing rod 31 can remain smooth without the need to set a structure for being connected to the installation part 211. The detachable connection between the installation part 211 and the fixing rod 31 can have various possible forms, such as threaded connection, snap connection, magnetic attraction, etc.

More specifically, the fixing rod 31 comprises a rod body 311 and a light guide barrel 312, wherein the light guide barrel 312 is integrally connected to the rod body 311, and the light guide barrel 312 is located in front of the camera element 40 and the light source 50, thereby guiding the light emitted by the light source 50.

The rod body 311 in this embodiment can also form as a barrel, and a diameter of the light guide barrel 312 is smaller than a diameter of the rod body 311. The camera element 40 is disposed in the rod body 311 without extending into the light guide barrel 312, and the light guide barrel 312 is also located in front of the light source 50. The light guide barrel 312 correspondingly forms a light guide wall 3121 on its inner wall, and the light guide wall 3121 forms a light guide channel 3122 and forms an opening 3123 communicating with the light guide channel 3122 at the front end. As a result, a portion of the light from the light source 50 can directly project into the ear through the opening 3123, and another portion of the light is reflected by the light guide wall 3121 and guided into the ear and project to an end of the ear spoon assembly 20 through the light guide channel 3122 and the opening 3123. Therefore, the light from the light source 50 is uniformly guided to the position that needs to be illuminated, and the light guide barrel 312 prevents external stray light from entering the field of view of the camera element 40, thereby reducing glare or dark spots and providing the user with a clearer image on the display screen 11.

In other words, in this embodiment, the camera element 40 and the light source 50 are not disposed at the corresponding position of the opening 3123, but are positioned in the fixing rod 31 away from the opening 3123, so that the light emitted by the light source 50 can be effectively directed into the field of view of the camera element 40, and also avoid direct light from the external environment directly hitting the camera element 40, so that the camera element 40 can obtain clear image information of the corresponding opening 3123.

It is worth mentioning that the light guide barrel 312 is used to removably install the ear spoon assembly 20, and the camera element 40 does not extend into the light guide barrel 312, thereby avoiding damage to the camera element 40 due to compression during the installation of the installation part 211 of the rigid inner spoon 21 of the ear spoon assembly 20 onto the light guide barrel 312.

In addition, the rod body 311 of the fixing rod 31 has a circular top surface 3111 adjacent to the light guide barrel 312. The installation part 211 of the rigid inner spoon 21 has a circular bottom surface 2112 at the bottom end. When the installation part 211 of the rigid inner spoon 21 is assembled outside the light guide barrel 312, the circular bottom surface 2112 of the installation part 211 abuts against the circular top surface 3111 of the rod body 311, and the outer diameter of the circular installation part 211 is the same as the outer diameter of the rod body 311, so that the outer surface 2113 of the installation part 211 of the rigid inner spoon 21 is in contact with the outer surface 3112 of the rod body 311 to form a continuous columnar outer surface.

Correspondingly, the light guide wall 3121 of the light guide barrel 312 has excellent mirror reflection performance. For example, the material of the light guide barrel 312 is a material with high reflectivity, such as aluminum, nickel, silver, or the light guide barrel 312 is coated with aluminum film, nickel film, or silver film to form a mirror reflection surface on the light guide wall 3121. When the light emitted from the light source 50 is incident on the light guide wall 3121, it can be effectively reflected towards the opening 3123, and the light guide wall 3121 has good polishing performance, so that the light reflected from the ear to the light guide barrel 312 is reflected towards the camera element 40 without causing stray light that affects the image effect.

The light source 50 comprises a light source circuit board 51 and a plurality of light emitting elements 52. The light source circuit board 51 is arranged around the camera element 40 for installing the light emitting elements 52. The top of the light emitting elements 52 forms a light emitting surface 53. The camera element 40 comprises a camera body 41 and a connection circuit board 42. The top of the camera body 41 forms a lens end surface 43. The light emitting surface 53 of the light source 50 is aligned with or located behind the lens end surface 43 of the camera element 40, so that the light from the light source 50 is effectively emitted towards the opening 3123 of the light guide barrel 312 to illuminate the ear canal and the ear spoon assembly 20, thereby avoiding the generation of ineffective light directly towards the camera element 40 and the generation of stray light from the side of the light source 50 that is directed towards the camera element 40.

The light source circuit board 51 and the connection circuit board 42 can both be advantageously implemented as flexible circuit boards, which can be conveniently bent and extended in the fixing rod 31. The light source circuit board 51 and the connection circuit board 42 are electrically connected to each other and further connected to the display device 10, so that the camera element 40 and the light source 50 can be controlled through the display device 10.

The fixing assembly 30 further comprises a holder 33 for installing the camera element 40 and the light source 50. The light guide barrel 312 of the fixing rod 31 forms an annular step surface 3124 adjacent to the position of the handle 32. The holder 33 comprises an annular end surface 331, which is adhered to the step surface 3124 by adhesive to assemble the holder 33 in the handle 32. The holder 33 also forms a receiving cavity 332 for accommodating the camera element 40. The connection circuit board 42 can pass through the holder 33, so as to be electrically connect to the display device 10.

Preferably, an inner surface 333 of the holder 33 has the same inner diameter as the light guide wall 3121 of the light guide barrel 312. When the annular end surface 331 of the holder 33 is adhered to the step surface 3124, the inner surface 333 of the holder 33 and the light guide wall 3121 of the light guide barrel 312 form a continuous tubular inner wall, which is used to guide and reflect the light emitted by the light source 50.

The flexible outer spoon 22 is detachably fitted outside the rigid inner spoon 21, and an end edge 2201 of the flexible outer spoon is used to contact and clean the earwax, and a center position 2202 is coaxial with a center 431 of the lens end surface 43 of the camera element 40, that is, coaxial with the central axis X of the camera element 40, so that the user can accurately judge the position of the end edge 2201 of the flexible outer spoon 22 in the image and facilitate the user to operate the ear cleaning arrangement 100 to clean the earwax accurately, and avoid scratching the ear canal and causing infection by the ear spoon assembly 20.

The light emitting elements 52 of the light source 50 are evenly distributed around the camera element 40, and these light emitting elements 52 comprise two middle light emitting elements 521 and 522 located at two ends of the diameter of the lens end surface 43 of the camera element 40, that is, the two light emitting elements located on the left and right sides of the lens end surface 43. The light emitting center positions of these two middle light emitting elements 521 and 522 are in the same straight line as the central end face 431 of the lens 43 of the camera element 40, and also is in the same plane with the end of the ear spoon assembly 20, that is, the end edge 2201 of the flexible outer spoon 22, so as to ensure that the center of the end of the ear spoon assembly 20 and the earwax in the ear are in the center of the field of view of the camera element 40, making it easier for the user to operate the ear spoon assembly 20 to aim at and clean the earwax.

That is to say, the two middle light emitting elements 521 and 522 respectively emit light, so that the earwax appearing in the field of view of the camera element 40 is exactly located at the center position of the end of the ear spoon assembly 20 in the field of view, rather than on a position deviated from the center. Therefore, in the circular image field of view of the display device 10, when the earwax image is displayed in the center of the image field of view, the user can precisely aim at and clean the earwax using the center position 2202 of the end edge 2201 of the flexible outer spoon 22.

The flexible outer spoon 22 comprises a flexible spoon body 221 and an extension part 222, wherein the flexible spoon body part 221 is integrally extended from the extension part 222. The flexible spoon body part 221 comprises a spoon bottom 2211 and a flange part 2212 that is integrally extended from the spoon bottom 2211. The flange part 2212 and the spoon bottom 2211 form a groove 2213 for accommodating earwax. The end of the flange part 2212 forms the end edge 2201 of the flexible outer spoon 22, and the end edge 2201 of the flexible outer spoon 22 is parallel and coplanar with the two middle light emitting elements 521 and 522, and the center position 2202 of the end edge 2201 is coaxial with the center 431 of the lens end surface 43 of the camera element 40.

The flexible outer spoon 22 has an installation channel 223 which extends in the extension part 222 and the flexible spoon body part 221 for installing the rigid inner spoon 21. The inner spoon body 212 of the rigid inner spoon 21 comprises a rigid spoon body 2121 and a connection part 2122. The connection part 2122 is integrally extended from the installation part 211, and the rigid spoon body 2121 is integrally extended from the connection part 2122.

The rigid spoon body 2121 of the inner spoon body 212 of the rigid inner spoon 21 has an end 21211. When the end 21211 of the rigid spoon body 2121 abuts against the end 2231 of the installation channel 223 of the flexible outer spoon 22, the end edge 2201 of the flange part 2212 of the flexible spoon body part 221 is precisely positioned at the center 2202 of the end edge 2201 and the center 431 of the lens end surface 43 of the camera element 40, and is in the same plane as the center positions of the two middle light emitting elements 521 and 522 and the center 431 of the lens end surface 43 of the camera element 40.

With reference to FIGS. 3 to 8, when the user can hold the handle 32 to guide the end 2201 of the ear spoon assembly 20 into their ear, and the light emitted by the light source 50 is projecting into the ear. The camera element 40 captures the image of the flexible outer spoon 22 of the ear spoon assembly 20 and the inside of the ear, and displays it on the display screen 11 of the display device 10. The end 2201 of the flexible outer spoon 22 of the ear spoon assembly 20 is located at the center of the circular image field of view, making it convenient to scrape the earwax in the ear into the groove 2213 of the flexible spoon body part 221 and clean it out of the ear along with the ear spoon assembly 20.

In a preferred embodiment of the present invention, the smart terminal 10 includes a processor 11 and a display device 12, such as a smartphone, smartwatch, tablet, computer, or other devices. In another embodiment of the present invention, the processor 11 may be integrated with the camera element 40. In a preferred embodiment of the present invention, the smart terminal further comprises a storage device 13 for storing information. The smart terminal 10 is communicatively connected to the ear cleaning arrangement 100 through the installation of an application (APP). The application installed on the smart terminal 10 is implemented on the processor 11, the display device 12, and the storage device 13. The application is implemented on the processor 11 to control the display device 12 to display the operation interface. Preferably, the display device 12 is display screen.

Figure 3:
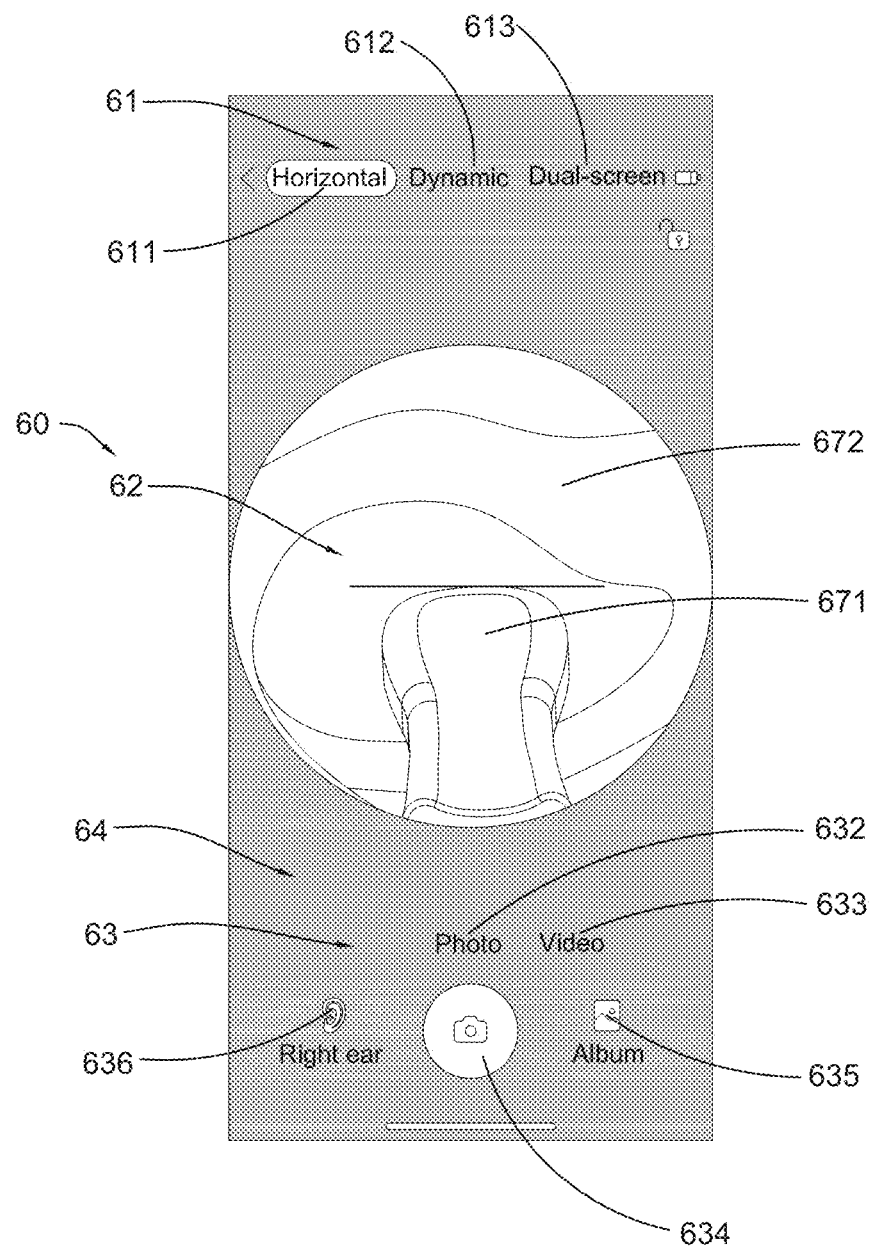
FIG. 3 and FIG. 4 illustrate schematic views of an operation interface of the ear cleaning arrangement according to an embodiment of the present application.
Figure 4:
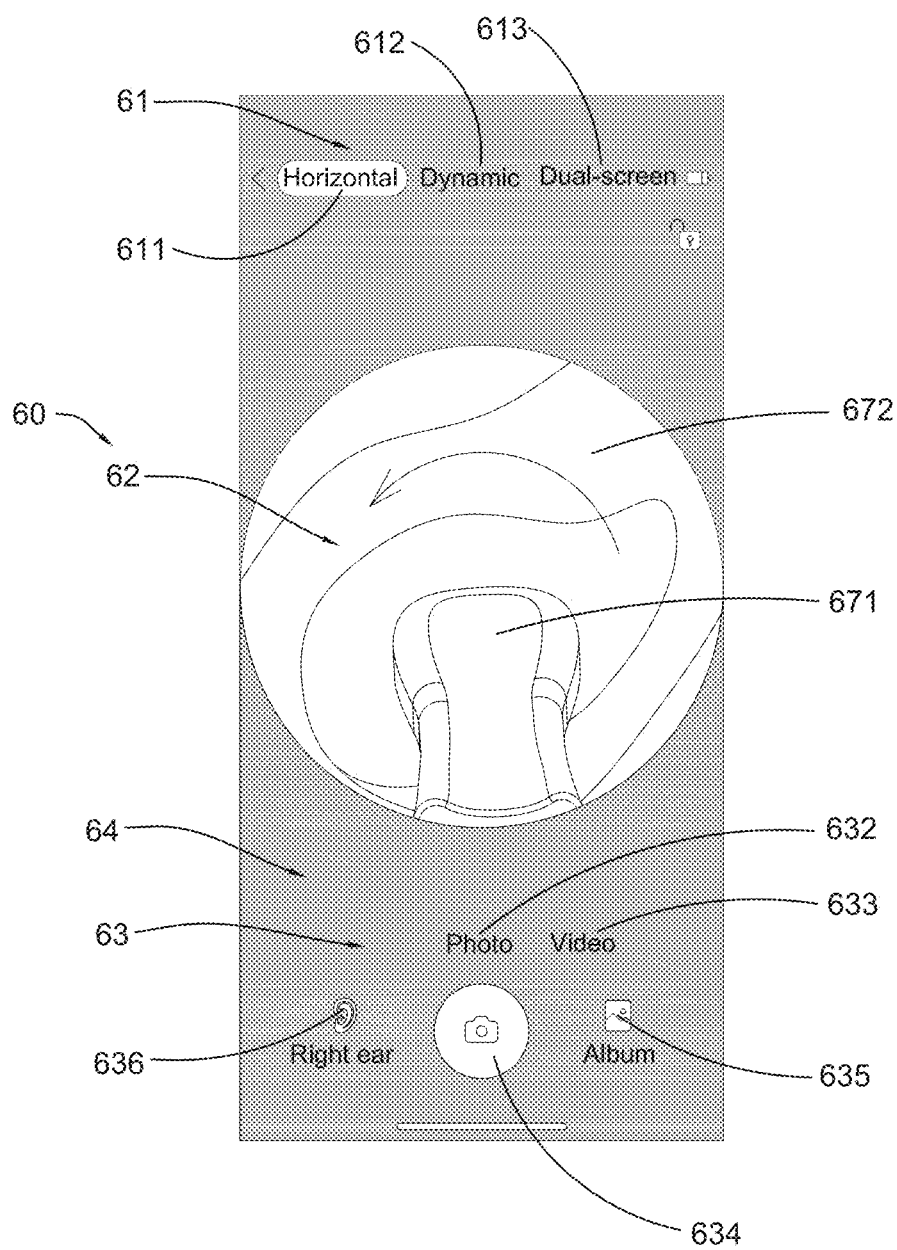
Figure 5:
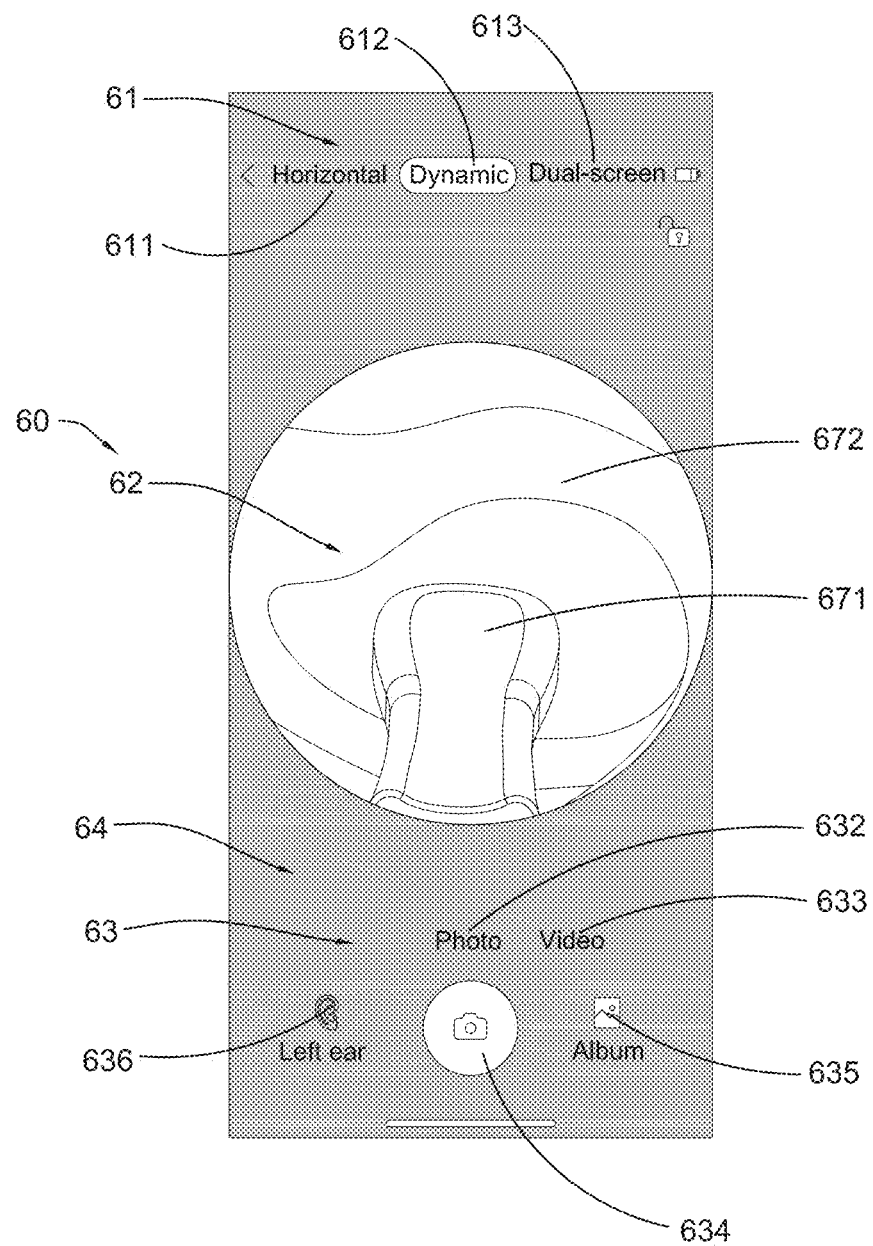
FIG. 5 and FIG. 6 are schematic views of an operation interface of the ear cleaning arrangement according to an embodiment of the present application.
Figure 6:
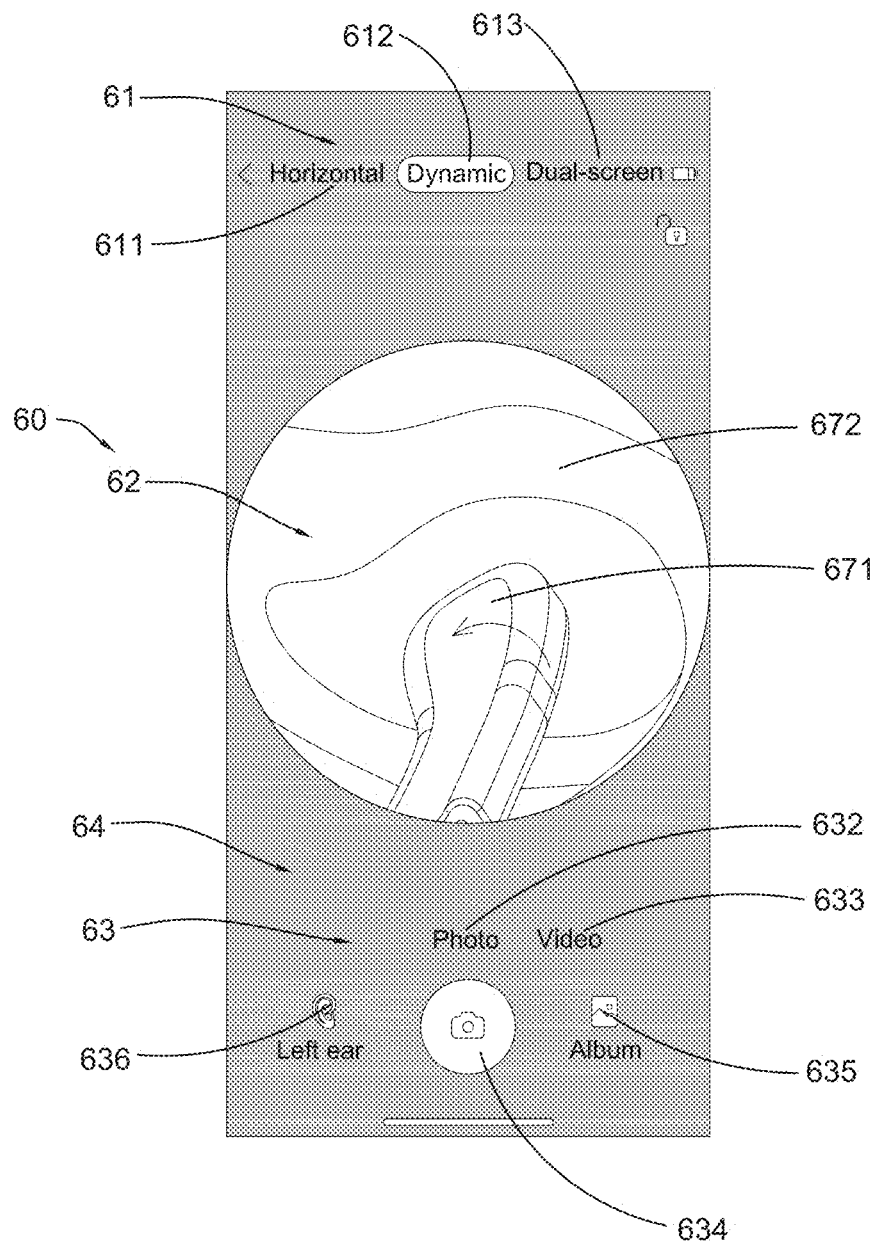
Figure 7:
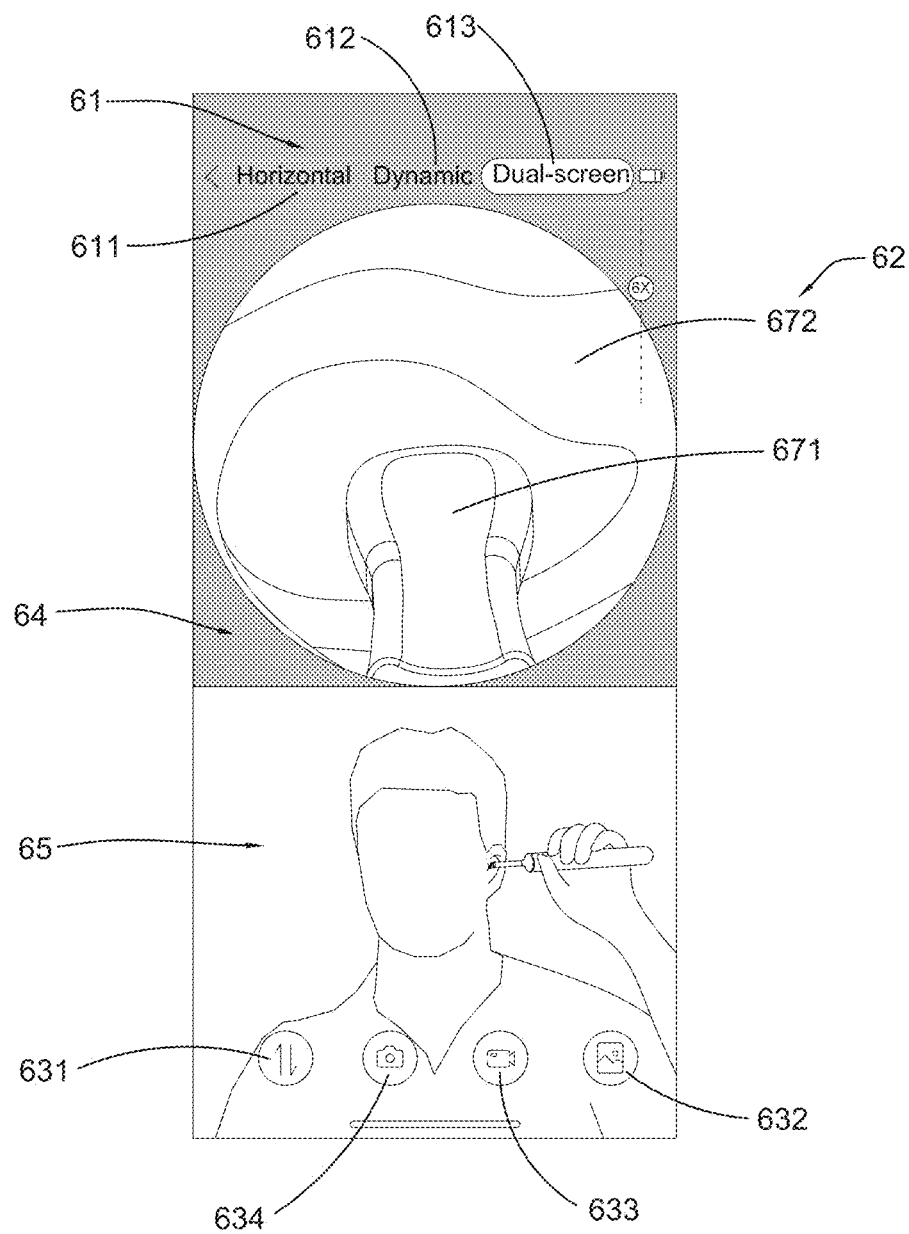
FIG. 7 is a schematic view of a split-screen operation interface of the ear cleaning arrangement according to a preferred embodiment of the present application.
Figure 8:
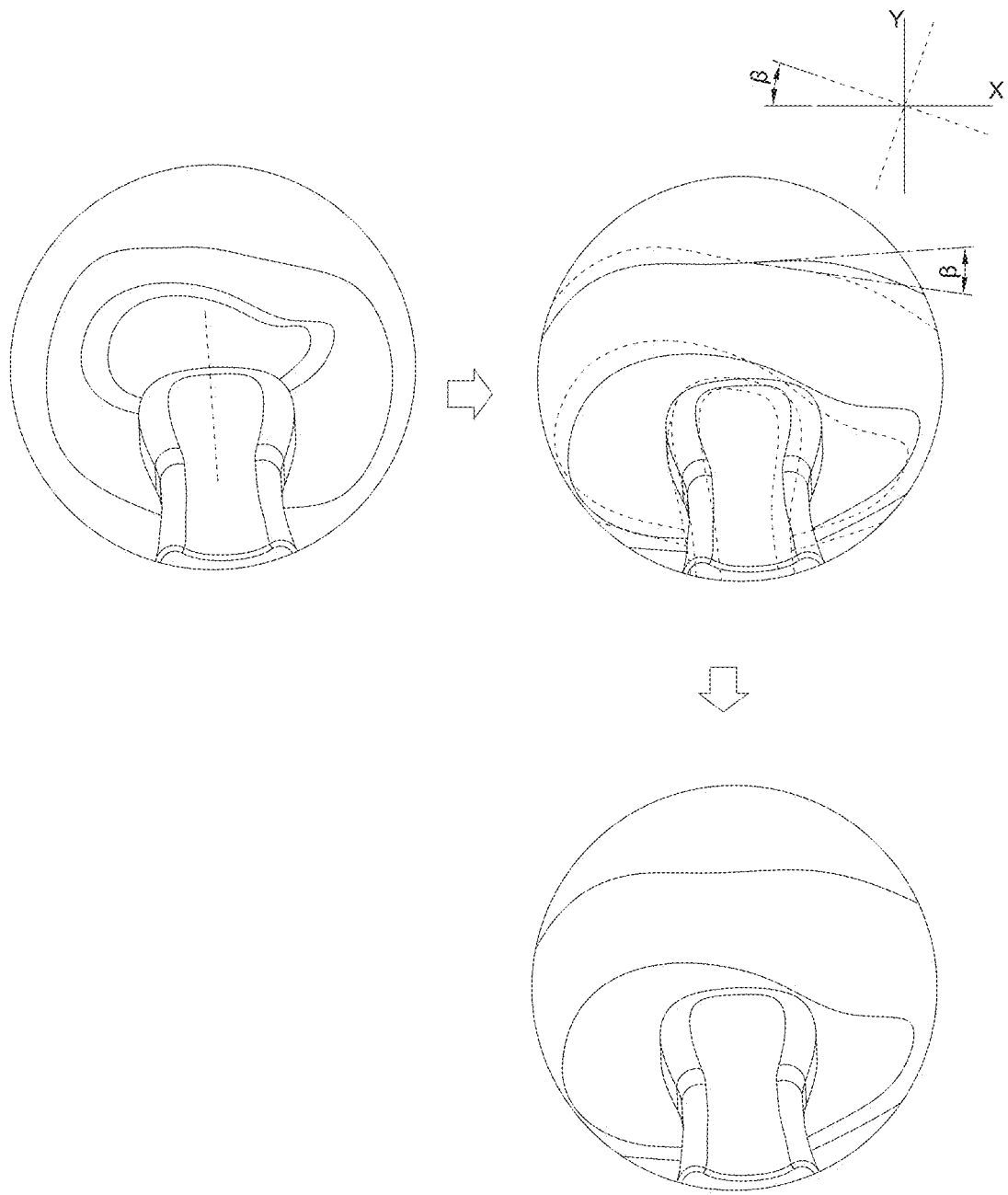
FIG. 8 is a schematic view of the ear cleaning arrangement entering the ear canal according to a preferred embodiment of the present application.
Figure 9:
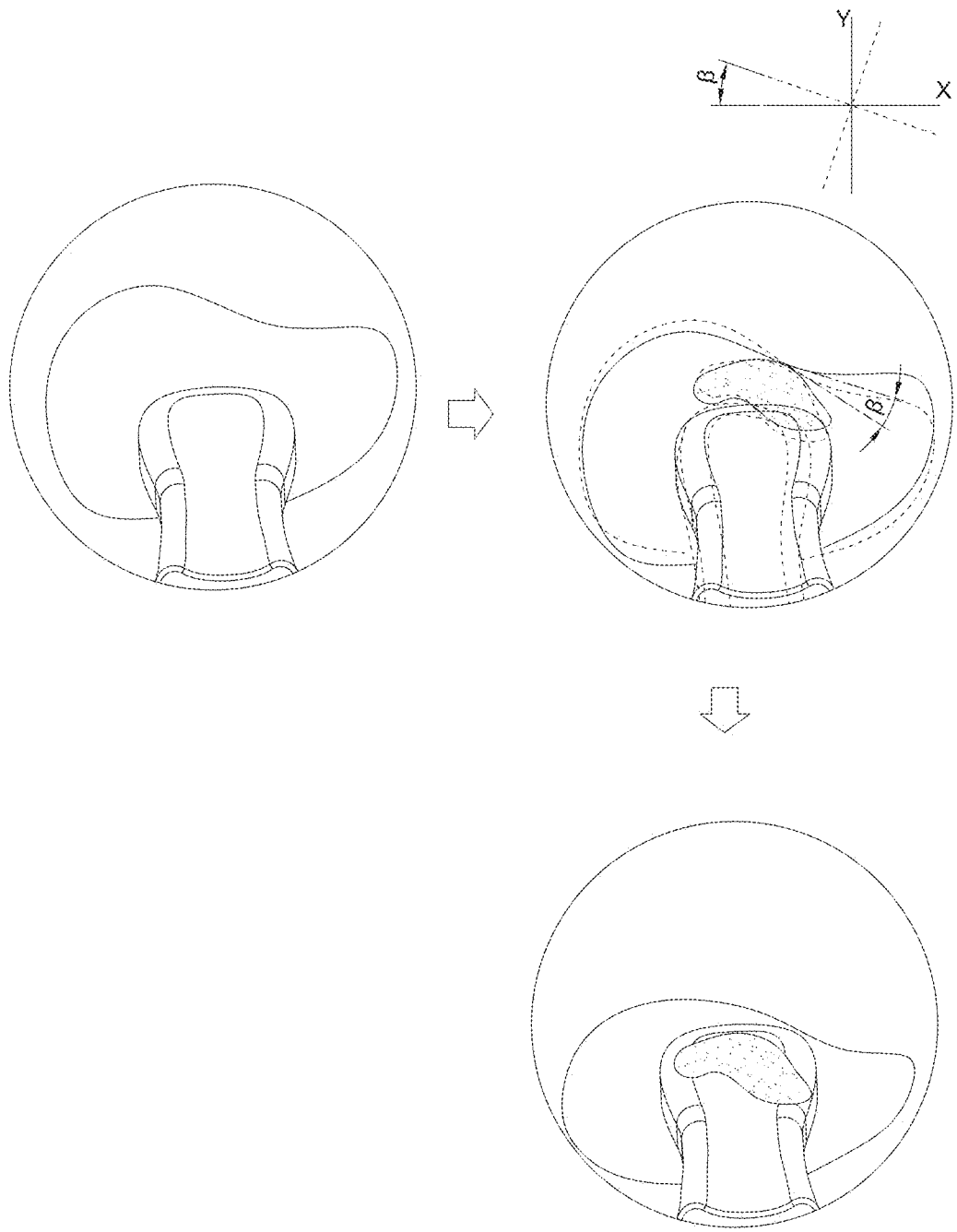
FIG. 9 is a schematic view of the ear cleaning arrangement cleaning the ear canal according to a preferred embodiment of the present application.
Figure 10:
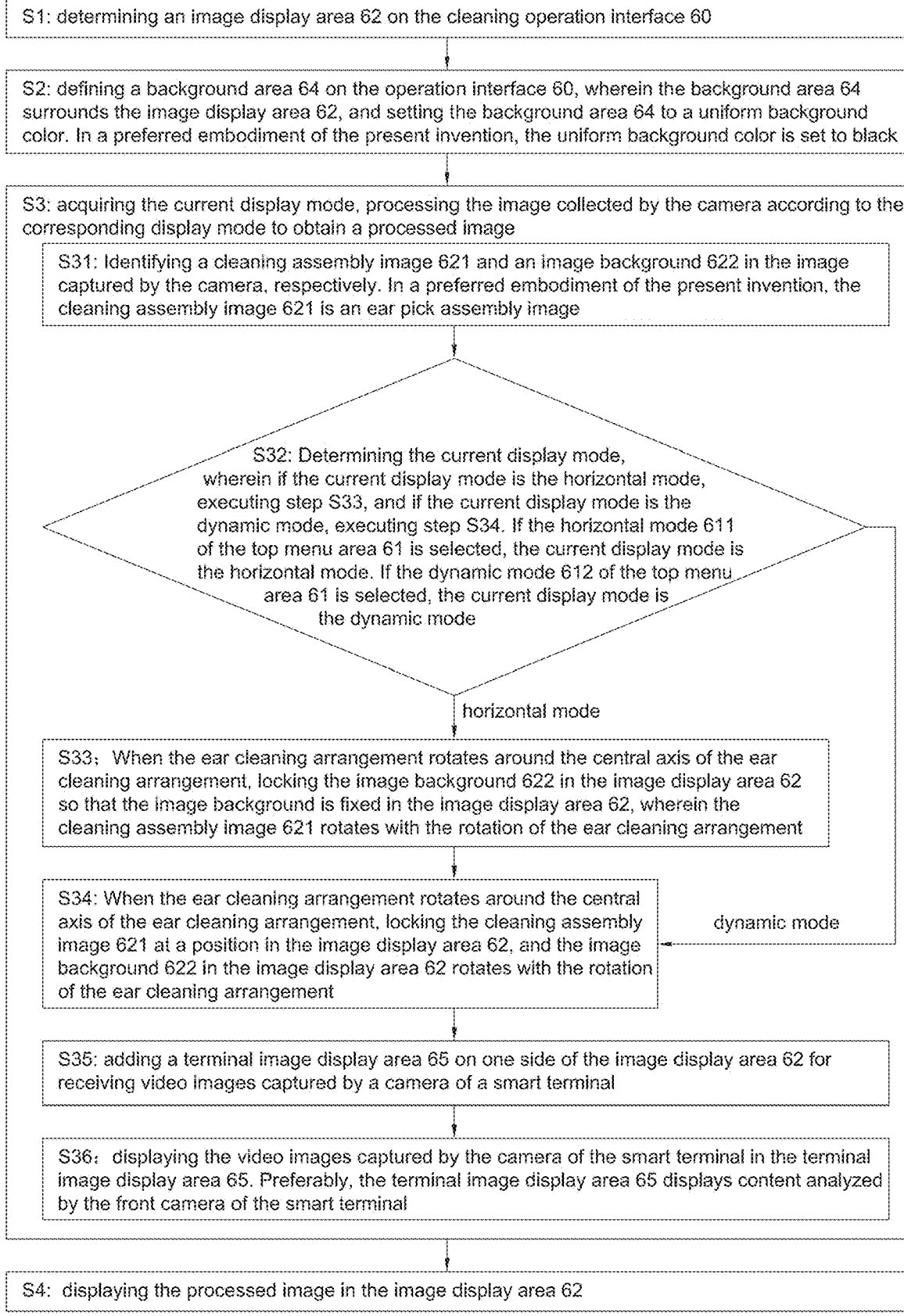
FIGS. 10, 11, and 12 are flowcharts of an image processing method for forming a split-screen operation interface of the ear cleaning arrangement according to a preferred embodiment of the present application.
Figure 11:
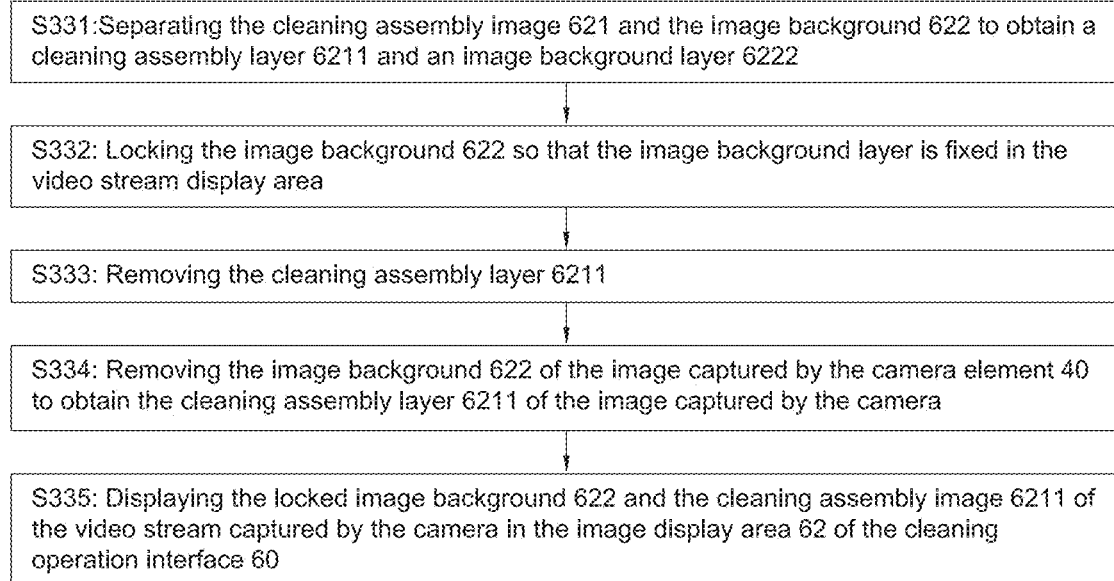
Figure 12:
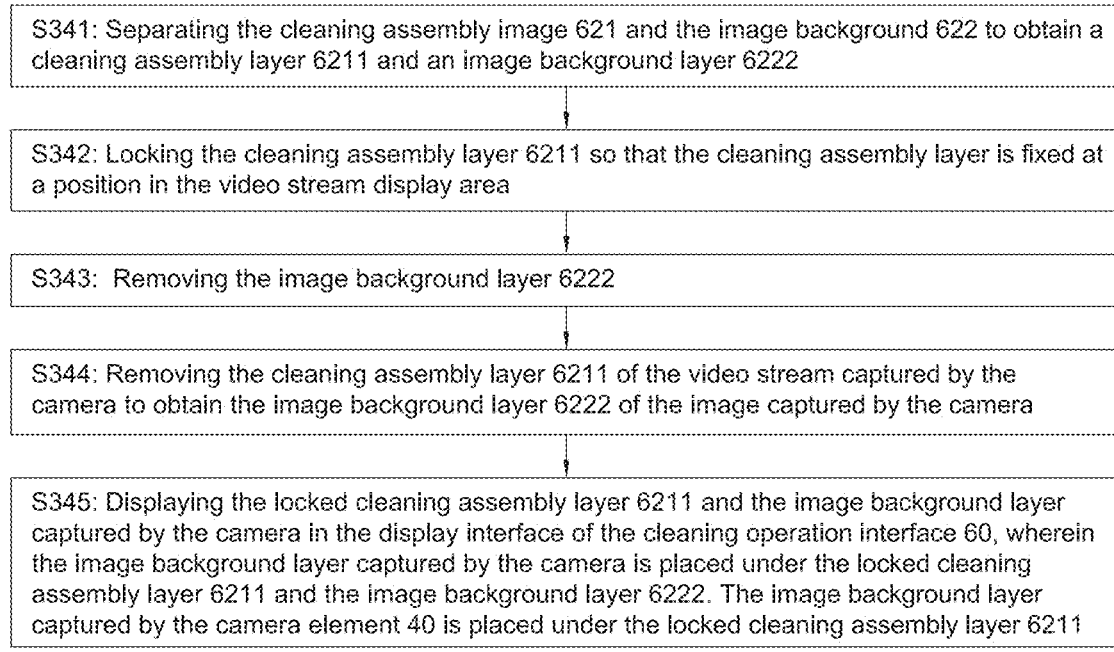
Figure 15:
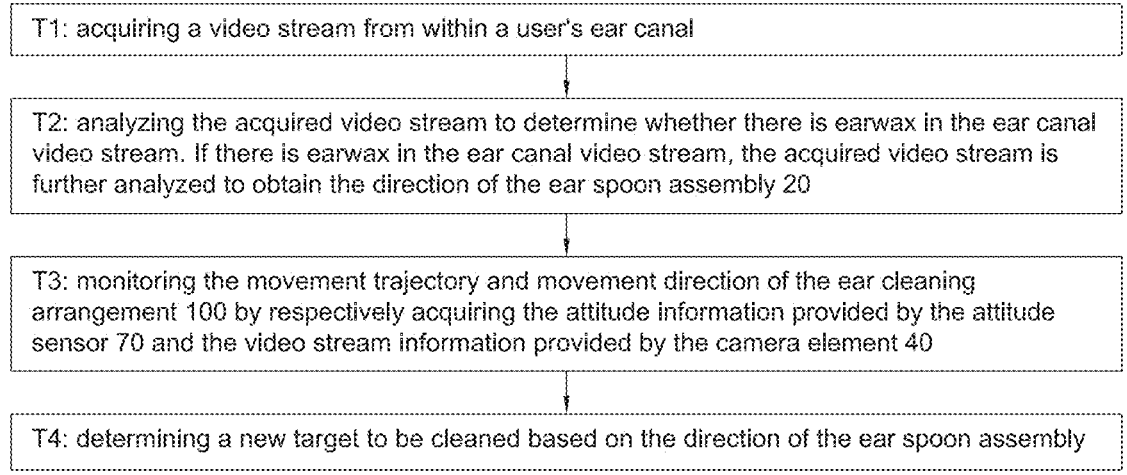
FIG. 15 is a flowchart of an image processing method of the ear cleaning arrangement according to a preferred embodiment of the present application.
Figure 16:
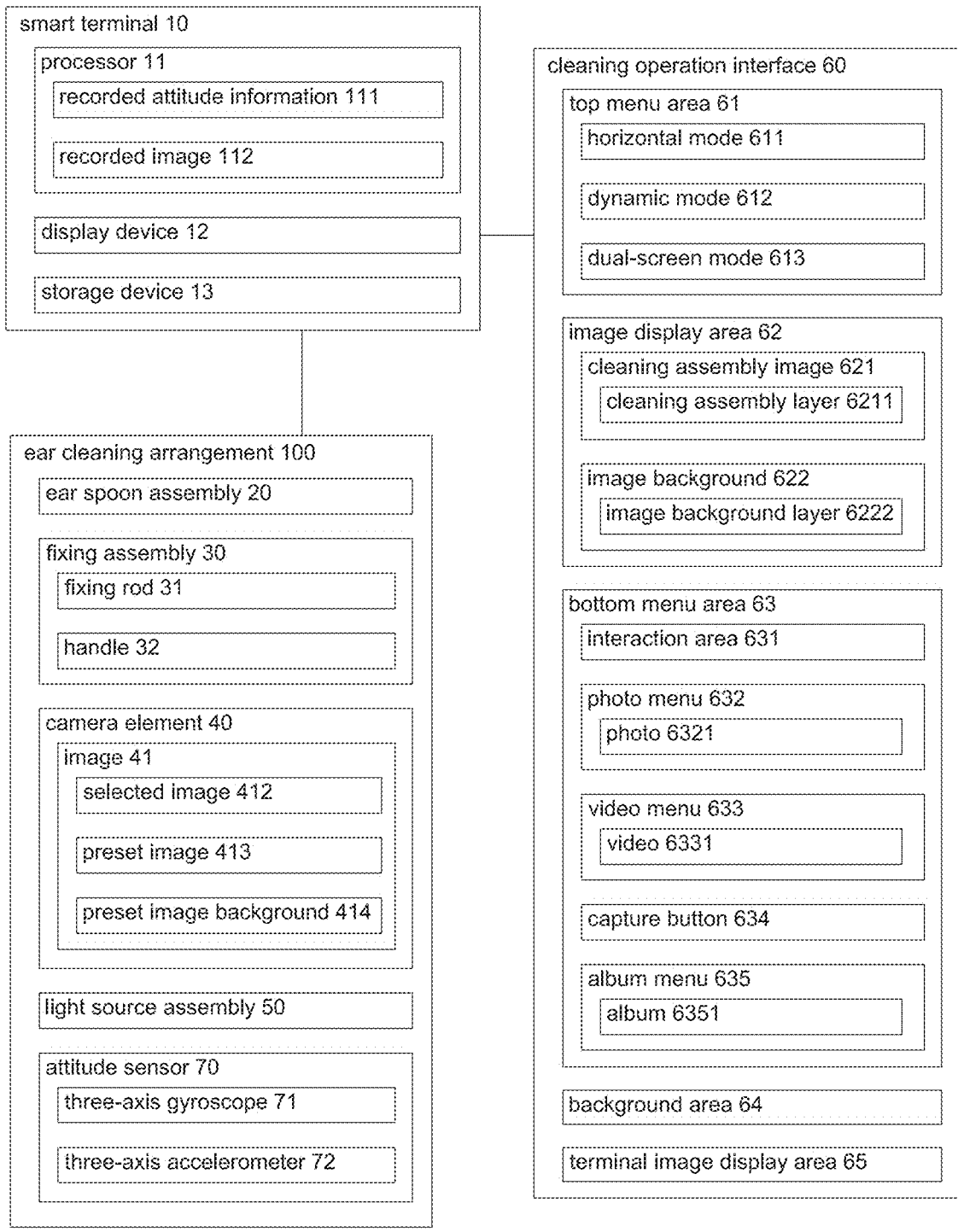
FIG. 16 is a structural block diagram of the ear cleaning arrangement according to a preferred embodiment of the present application.

FIGS. 3 and 4 show a cleaning operation interface 60 for the visual ear cleaning arrangement during ear cleaning in a preferred embodiment of the present invention. The cleaning operation interface 60 is operated on the smart terminal 10, and the cleaning operation interface 60 is displayed through the display device 12 of the smart terminal 10. The cleaning operation interface 60 further comprises a top menu area 61, an image display area 62, and a bottom menu area 63. The image display area 62 is disposed below the top menu area 61. In a preferred embodiment of the present invention, the image display area 62 is set to a circular shape. The cross-section of a human ear canal is roughly circular, and setting the image display area 62 to a circular shape can match the shape of the cross-section of the ear canal, thereby helping the user focus on the operation of removing earwax in the ear canal. Furthermore, the area between the circular image display area 62 and the top menu area 61 is defined as a background area 64. Preferably, the background area 64 uses black as the background color to help the user focus on the image display area 62.

The top menu area 61 is used to display the mode selection menu. The top menu area 61 further comprises a horizontal mode 611 and a dynamic mode 612. It is worth mentioning that, the image display area 62 displays the image captured by the camera element 40. The image captured by the camera element 40 includes an end portion of the ear spoon assembly 20. The end portion is away from the fixing rod 31. The image display area 62 displays the end portion of the ear spoon assembly 20. In other words, the image display area 62 further includes an ear spoon assembly display section 671 and an image display section 672, with the ear spoon assembly display section 671 adjacent to the image display section 672. When the horizontal mode 611 is selected, the horizontal mode is activated. When the visual ear cleaning arrangement rotates, the currently displayed image in the image display section 672 is locked, while the ear spoon assembly display section 671 rotates with the rotation of the ear cleaning arrangement 100. When the horizontal mode 611 is deactivated, the currently displayed image in the image display section 672 is unlocked, and when the visual ear cleaning arrangement rotates, both the image display section 672 and the ear spoon assembly display section 671 rotate together. When the dynamic mode 612 is selected, the dynamic mode is activated. The ear spoon assembly display section 622 is locked. In a preferred embodiment of the present invention, the ear spoon assembly display section 671 is locked at the bottom of the image display area 62. In the dynamic mode 612, when the visual ear cleaning arrangement 100 rotates about its central axis, the camera element 40 captures images in a rotating manner. However, since the ear spoon assembly display section 671 is locked, it remains at the bottom of the image display area 62, and the image display section 672 displays the images captured by the rotating camera element 40. Thus, the image display section 672 displays rotating images. The top menu area 61 further includes a magnification adjustment section 614. The magnification adjustment section 614 is used to adjust the magnification of the image displayed in the image display area 62.

It is worth mentioning that the top menu area 61 further comprises a dual-screen mode 613. When the dual-screen mode 613 is selected, the cleaning operation interface 60 further includes a terminal image display area 65. In a preferred embodiment of the present invention, the terminal image display area 65 is disposed below the image display area 62.

Specifically, the image display area 62 and the terminal image display area 65 are arranged below the top menu area. The terminal image display area 65 displays video images captured by a camera of a smart terminal. In a preferred embodiment of the present invention, the terminal image display area 65 displays images captured by the front camera of a smartphone. It is worth mentioning that the positions of the terminal image display area 65 and the image display area 62 can be interchanged. When using the dual-screen mode, the image display area 62 displays the image of the user's ear canal, while the terminal image display area 65 shows the user's posture when using the visual ear cleaning arrangement. In this manner, the user can refer to their posture when using the visual ear cleaning arrangement to control the device for cleaning their ear, thereby facilitating the use of the visual ear cleaning arrangement for ear canal cleaning.

The bottom menu area 63 is disposed at the bottom of the cleaning operation interface 60. The bottom menu area 63 further comprises an interaction area 631. When the interaction area 631 is clicked, the positions of the image display area 62 and the terminal image display area 65 are swapped. The bottom menu area further comprises a photo menu 632, a video menu 633, a capture button 634, and an album menu 635. When the photo menu 632 is selected, clicking the capture button 634 captures the current image collected by the camera element 40 as a photo 6321. The photo is stored in an album 6351. By clicking the album menu 635, the user can access the album 6351 to view the photo 6321. When the video menu 633 is selected, clicking the capture button 634 records the image collected by the camera as a video 6331. The video 6331 is stored in the album 6351. In a preferred embodiment of the present invention, the bottom menu area further comprises an ear display section 636. The ear display section 636 is used to display the ear currently being cleaned.

The present invention provides an image processing method for an ear cleaning arrangement, comprising the following steps:

S1: determining an image display area 62 on the cleaning operation interface 60. In a preferred embodiment of the present invention, the image display area 62 is circular, and the images in the image display area 62 are sourced from the camera element 40. The image display area 62 is used to display the video stream collected by the camera element 40.

S2: defining a background area 64 on the operation interface 60, wherein the background area 64 surrounds the image display area 62, and setting the background area 64 to a uniform background color. In a preferred embodiment of the present invention, the uniform background color is set to black.

S3: acquiring the current display mode, processing the image collected by the camera according to the corresponding display mode to obtain a processed image; and S4: displaying the processed image in the image display area 62.

Wherein, step S3 further comprises the following steps:

S31: Identifying a cleaning assembly image 621 and an image background 622 in the image captured by the camera, respectively. In a preferred embodiment of the present invention, the cleaning assembly image 621 is an ear spoon assembly image.

S32: Determining the current display mode, wherein if the current display mode is the horizontal mode, executing step S33, and if the current display mode is the dynamic mode, executing step S34. If the horizontal mode 611 of the top menu area 61 is selected, the current display mode is the horizontal mode. If the dynamic mode 612 of the top menu area 61 is selected, the current display mode is the dynamic mode.

S33: When the ear cleaning arrangement rotates around the central axis of the ear cleaning arrangement, locking the image background 622 in the image display area 62 so that the image background is fixed in the image display area 62, wherein the cleaning assembly image 621 rotates with the rotation of the ear cleaning arrangement.

S34: When the ear cleaning arrangement rotates around the central axis of the ear cleaning arrangement, locking the cleaning assembly image 621 at a position in the image display area 62, and the image background 622 in the image display area 62 rotates with the rotation of the ear cleaning arrangement.

Wherein, step S33 further comprises the following steps:

S331: Separating the cleaning assembly image 621 and the image background 622 to obtain a cleaning assembly layer 6211 and an image background layer 6222.

S332: Locking the image background 622 so that the image background layer is fixed in the video stream display area.

S333: Removing the cleaning assembly layer 6211.

S334: Removing the image background 622 of the image captured by the camera element 40 to obtain the cleaning assembly layer 6211 of the image captured by the camera.

S335: Displaying the locked image background 622 and the cleaning assembly image 6211 of the video stream captured by the camera in the image display area 62 of the cleaning operation interface 60.

Wherein, step S34 further comprises the following steps:
S341: Separating the cleaning assembly image 621 and the image background 622 to obtain a cleaning assembly layer 6211 and an image background layer 6222.

S342: Locking the cleaning assembly layer 6211 so that the cleaning assembly layer is fixed at a position in the video stream display area.

S343: Removing the image background layer 6222.

S344: Removing the cleaning assembly layer 6211 of the video stream captured by the camera to obtain the image background layer 6222 of the image captured by the camera.

S345: Displaying the locked cleaning assembly layer 6211 and the image background layer captured by the camera in the display interface of the cleaning operation interface 60, wherein the image background layer captured by the camera is placed under the locked cleaning assembly layer 6211 and the image background layer 6222. The image background layer captured by the camera element 40 is placed under the locked cleaning assembly layer 6211.

Step S32 can be replaced by step S32A.

Step S32A: determining the current display mode, wherein if the current display mode is the horizontal mode, executing step S33, if the current display mode is the dynamic mode, executing step S34, and if the current display mode is the dual-screen mode, executing step S35.

Step S35: adding a terminal image display area 65 on one side of the image display area 62 for receiving video images captured by a camera of a smart terminal.

Step S36: displaying the video images captured by the camera of the smart terminal in the terminal image display area 65. Preferably, the terminal image display area 65 displays content analyzed by the front camera of the smart terminal.

In a preferred embodiment of the present invention, when the user uses the ear cleaning arrangement 100 to clean their ear, the ear cleaning arrangement 100 is communicatively connected to the smart terminal 10. The communication methods for the ear cleaning arrangement 100 include WiFi, Bluetooth, and other methods. Specifically, the user places the ear cleaning arrangement 100 in front of them to view the video stream captured by the camera element 40. The user positions the ear cleaning arrangement 100 at the height of their ear. When the ear spoon assembly 20 of the ear cleaning arrangement 100 faces the user's ear in a horizontal posture, the posture of the ear cleaning arrangement 100 is defined as a horizontal posture. If the video stream captured by the camera element 40 shows the ear spoon assembly 20 aligned with the user's ear canal, the user only needs to move the ear spoon assembly 20 horizontally towards the ear canal to insert the ear spoon assembly 20 into the user's ear canal. During the movement of the ear cleaning arrangement 100, the ear cleaning arrangement 100 may shake. The shaking of the ear cleaning arrangement 100 causes the video stream captured by the camera element 40 to shake, meaning that the video stream displayed in the image display area 62 keeps changing, thereby failing to provide visual assistance to the user.

In a preferred embodiment of the present invention, the ear cleaning arrangement 100 further comprises an attitude sensor 70. The current attitude information of the ear cleaning arrangement 100 is acquired by the attitude sensor 70. The attitude sensor 70 transmits the acquired attitude information to the processor 11 for processing. The current attitude angle and azimuth angle of the ear cleaning arrangement 100, as well as other relevant attitude information, are recorded. Preferably, the current rotation angle and azimuth angle of the ear cleaning arrangement 100 are recorded in the smart terminal 10.

In a preferred embodiment of the present invention, the attitude sensor 70 comprises a three-axis gyroscope 71 and a three-axis accelerometer 72. The three-axis gyroscope 71 is used to provide rotation angle change data to measure angular velocity and determine the motion state of the object. The three-axis accelerometer 72 is used to obtain directional change data and acceleration information to determine the motion direction and position of the object. The method of acquiring motion direction, trajectory, and position using the three-axis gyroscope 71 and the three-axis accelerometer 72 is common. For example, when the camera element 40 captures a video stream, the three-axis gyroscope captures tt, tx, ty, and tz, where tt is defined as system time, and tx, ty, tz are the angular velocities in the x, y, and z directions of the three-axis gyroscope. By calculating quaternion angle integration based on tt, tx, ty, and tz, and converting the integration result into Euler angles and accumulating them, and finally converting the accumulated result back into quaternions, the rotation angle change data is obtained. For azimuth angle processing, by obtaining the projection vectors of the acceleration vector in the yz, zx, and xy planes from the video stream data captured by the camera element 40, and calculating the inclination angles in the X-axis, Y-axis, and Z-axis directions, the azimuth angle change data is obtained. Those skilled in the art will understand how to use the three-axis gyroscope 71 and the three-axis accelerometer 72 to obtain the current position, current attitude, movement direction, and movement trajectory of the ear cleaning arrangement.

The video stream captured by the camera element 40 of the ear cleaning arrangement 100 and the attitude information captured by the attitude sensor 70 of the ear cleaning arrangement 100 are transmitted to the smart terminal 10. The processor 11 of the smart terminal 10 processes the video stream captured by the camera element 40 and the attitude information, respectively.

The processor 11 controls the display device 12 to display the cleaning operation interface 60. The image display area 62 displays the video stream captured by the camera element 40. When the ear spoon assembly 20 of the ear cleaning arrangement 100 approaches the user's ear canal, if the video stream captured by the camera element 40 comprises the ear canal entrance, the video stream displayed in the image display area 62 comprises the ear canal entrance. The user operates the ear spoon assembly 20 of the ear cleaning arrangement 100 to enter the ear canal based on the video stream displayed in the image display area 62. It is worth mentioning that when the user moves the ear spoon assembly 20 towards their ear canal, the processor 11 processes the received video stream transmitted from the camera element 40 to maintain the stability of the video stream in the image display area 62.

The attitude information of the ear cleaning arrangement 100 and the video stream captured by the camera of the ear cleaning arrangement 100 are recorded, resulting in recorded attitude information 111111 and recorded video stream information 411. The processor 11 analyzes the recorded video stream information.

Specifically, one frame from the video stream information is selected as a selected image 412 for analysis. The processor 11 identifies the content of the selected image. If the content of the selected image comprises an image of the ear canal entrance, the direction of the ear spoon assembly 20 in the selected image is further analyzed. If the direction of the ear spoon assembly 20 points to the ear canal entrance, the ear canal entrance is defined as a target to be entered. The recorded attitude information is used to determine the movement direction and position of the ear cleaning arrangement 100. That is to say, the ear spoon assembly 20 provides an indication function to indicate the target to be operated on.

As the ear spoon assembly 20 continues to move towards the ear canal entrance, the processor 11 receives the attitude information transmitted by the attitude sensor and the video stream images transmitted by the camera element 40. In a preferred embodiment of the present invention, the processor 11 obtains the current attitude information of the attitude sensor 70 based on the transmitted current attitude information, such as the current azimuth angle and/or rotation angle information of the ear cleaning arrangement 100. Rotation angle, also known as angular displacement, refers to the angle between the line connecting a point with the center and the line connecting the corresponding point after rotation with the rotation center when a figure rotates. Azimuth, also known as azimuthal angle, is the horizontal angle measured clockwise from the north direction line to the target direction line. The attitude information of the ear cleaning arrangement 70 can be represented by information such as azimuth and rotation angles.

The processor 11 compares the current attitude information of the attitude sensor 70 with the recorded attitude information. If the attitude change is within a preset range, it is determined that the current movement direction of the ear cleaning arrangement 100 is consistent with the recorded direction. In a preferred embodiment of the present application, if the current movement direction of the ear cleaning arrangement 100 is consistent with the recorded direction, the processor 11 sets the selected image 412 as the image displayed in the image display area 62.

If the attitude change is outside the preset range, it is determined that the current movement direction of the ear cleaning arrangement 100 is inconsistent with the recorded direction. In a preferred embodiment of the present invention, the processor 11 processes the current view captured by the camera.

The processor 11 displays the selected image 412 as the current image in the image display area 62. It is worth mentioning that if the ear cleaning arrangement moves in the recorded direction, the selected image 412 will be updated at a preset time. In other words during the movement of the ear cleaning arrangement 100 towards the ear canal, the processor 11 selects one frame from the current video stream as the selected image 412 for updating at the preset time. The processor 11 displays the updated selected image 412 in the image display area 62. In this way, the image display area 62 synchronously displays the images captured by the camera element 40. If the azimuth change is outside the preset range, it is determined that the current movement direction of the ear cleaning arrangement 100 is inconsistent with the recorded direction. The processor 11 then reacquires the attitude information of the ear cleaning arrangement captured by the attitude sensor 70 and the video stream information captured by the camera element 40.

After the ear cleaning arrangement 100 enters the ear canal, the camera element 40 of the ear cleaning arrangement 100 captures the video stream inside the user's ear and transmits it to the processor 11 for processing. The processor 11 analyzes whether the video stream includes earwax. Specifically, the processor 11 selects one frame from the captured video stream as the selected image 412. The processor 11 further analyzes whether the selected image 412 includes earwax. If the selected image 412 further analyzes the direction of the ear spoon assembly 20 in the selected image 412, and the ear spoon assembly 20 points to the earwax, the user only needs to control the ear spoon assembly 20 to move towards the earwax in the current direction, and the ear spoon assembly 20 can contact the earwax. By operating the ear spoon assembly 20, the earwax can be removed. The attitude sensor 70 of the ear cleaning arrangement 100 acquires the current attitude information of the ear cleaning arrangement 100. The camera element 40 of the ear cleaning arrangement 100 captures the current video stream information. The processor 11 records the current attitude information and the current captured video stream information of the ear cleaning arrangement 100, obtaining the recorded attitude information 111 and recorded video stream information 411. When the ear spoon assembly 20 of the ear cleaning arrangement 100 moves, the processor 11 acquires the current attitude information from the attitude sensor 70. The processor 11 analyzes the current attitude information and the recorded attitude information 111 recorded attitude information 111. If the change in the movement direction of the ear cleaning arrangement 100 is within the preset range, the processor 11 determines that the movement direction of the ear cleaning arrangement is consistent with the recorded direction. Within a preset time, the processor 11 uses the recorded video stream information 411 for display in the image display area 62. Outside the preset time, the processor 11 acquires the current attitude information of the ear cleaning arrangement and compares it with the recorded attitude information 111. Through the analysis of the processor 11, if the azimuth of the current attitude information is consistent with the azimuth of the recorded attitude information 111, the current attitude information is updated to the recorded attitude information 111. The processor 11 acquires the current video stream information from the camera element 40. The processor 11 updates the current video stream information to the recorded video stream information 411. The processor 11 displays the updated recorded video stream information in the image display area 62. The user operates the ear spoon assembly 20 to clean the ear canal based on the video stream displayed in the image display area 62.

It is worth mentioning that, in another preferred embodiment of the present invention, the processor 11 is configured to set a preset time. The preset time is set by the user according to the situation. The processor 11 obtains the current attitude information of the ear cleaning arrangement 100 through the attitude sensor 70. The processor 11 obtains the current video stream information through the camera element 40. The processor 11 receives the current video stream transmitted from the camera element 40 and the current attitude information transmitted from the attitude sensor 70. The current video stream transmitted by the camera element 40 is recorded to obtain recorded video stream information 112. The processor 11 selects one frame from the recorded video stream information 112 as the selected image 412. The processor 11 further analyzes the selected image 412 to determine the corresponding image of the ear spoon assembly 20 and the target pointed to by the image of the ear spoon assembly 20. The target pointed to by the image of the ear spoon assembly 20 is defined as the target to be processed. For example, if the selected image 412 includes the entrance of the ear canal and the ear spoon assembly 20 points to the entrance of the ear canal, the entrance of the ear canal is defined as the target to be processed. If the selected image 412 identifies earwax and the ear spoon assembly 20 points to the earwax, the earwax is defined as the target to be processed. It is worth mentioning that, as the ear spoon assembly 20 approaches the earwax, the processor 11 obtains the current attitude information from the attitude sensor 70. The processor 11 compares the current attitude with the recorded attitude information. It is worth mentioning that once the target to be processed is determined, the ear spoon assembly 20 only needs to move along the direction pointed to by the ear spoon assembly 20 to reach the target to be processed. As the ear spoon assembly 20 moves toward the target to be processed, the processor 11 obtains the movement direction of the ear cleaning arrangement 100 through the attitude sensor 70. The processor 11 obtains the current video stream through the camera element 40. If the movement direction of the ear spoon assembly 20 is within the preset range of the change in the recorded attitude information, the processor 11 determines that the movement direction of the ear spoon assembly 20 is consistent with the recorded movement direction. It is worth mentioning that the processor 11 obtains another current attitude information of the ear cleaning arrangement 100 at preset intervals through the attitude sensor 70. The other current attitude information is used to obtain the other current movement direction of the ear spoon assembly 20. The processor 11 obtains the other current video stream through the camera element 40. If the movement direction of the ear spoon assembly 20 is within the preset range of the change in the recorded attitude information, the processor 11 determines that the other current movement direction of the ear spoon assembly 20 is consistent with the recorded movement direction. The processor 11 further compares the recorded image 112, the current video stream, and the other current video stream to obtain the changes in the video stream.

In a preferred embodiment of the present invention, as the ear spoon assembly 20 moves toward the target to be processed, the camera element 40 gradually approaches the target to be processed. The target to be processed gradually enlarges in the video stream being captured. In other words, the area occupied by the target to be processed in each frame image gradually increases. In the displayed frame images, the pixel area occupied by the target to be processed gradually increases. The processor 11 identifies the pixel area occupied by the target to be processed in each frame image of the captured video stream. The processor 11 further analyzes the changes in the pixel area occupied by the processing target in adjacent frame images to obtain the image change characteristics. The processor 11 obtains the movement speed of the ear cleaning arrangement 100 through the attitude sensor 70. The processor 11 obtains a trend change characteristic based on the image change characteristics, the movement speed of the ear cleaning arrangement 100, and the time. In a preferred embodiment of the present invention, the target to be processed is the entrance of the ear canal and earwax. The process of the ear cleaning arrangement 100 entering the ear canal and the process of the ear cleaning arrangement 100 cleaning the earwax make image stabilization particularly important.

The processor 11 generates a preset image 413 after a preset time based on the trend change characteristic of the video stream. The processor 11 displays the preset image 413 in the image display area 62. By obtaining the changes in the image and generating the video stream after a preset time in advance, the problem of image shake caused by communication delay can be overcome.

Specifically, since the camera element 40 is disposed at one end of the fixing assembly 40, the camera element 40 moves together with the ear spoon assembly 20. That is to say, the ear spoon assembly 20 remains unchanged in the video stream captured by the camera element 40. In other words, the proportion of the ear spoon assembly 20 in the captured image remains unchanged. The processor 11 processes the selected image 412 to separate the image of the ear spoon assembly 20 as the cleaning assembly layer 6211. The background of the selected image 412 is used as the image background 622. The target to be processed is recorded in the image background 622. As the ear spoon assembly 20 moves toward the target to be processed, the camera element 40 moves toward the target to be processed. The proportion of the target to be processed in the video stream gradually increases in the image background 622. The processor 11 processes the image background 622 based on the changes in the video stream to obtain a preset image background 414.

The processor 11 further processes the preset image background 414 and the cleaning assembly layer 6211 to obtain the preset image 413. The preset image is displayed in the image display area 62.

Further, during the operation of the ear cleaning arrangement 60, one operating mode is that the ear cleaning arrangement 100 moves from the horizontal direction to the vertical direction, which is defined as the first operating mode. Another operating mode is that the ear cleaning arrangement moves from the vertical direction to the horizontal direction, which is defined as the second operating mode. Depending on the different operating modes, the corresponding method is used to adjust the video stream displayed in the image display area 62.

The image processing method for the first operating mode or the second operating mode comprises the following steps:

G1: acquiring a segment of video stream through the camera element 40, and selecting one frame image from the video stream as a selected image 412 through the processor 11. In another alternative embodiment, a frame image may also be captured as the selected image through the camera element 40 by the processor 11.

G2: analyzing the attitude information at the time point corresponding to the selected image 412 through the processor 11 to obtain rotation angle change data and azimuth angle change data.

G3: determining whether the operating mode corresponding to the selected image 412 is the first operating mode or the second operating mode. If it is the first operating mode, executing step G4. If it is the second operating mode, executing step G5.

G4: defining a preset angle β between a preset axis of the attitude sensor 70 and the horizontal direction, and determining whether |β-90| is less than or equal to a preset angle θ. If yes, executing step G5. If no, executing step G6. Preferably, the range of the preset angle θ is between 5 degrees and 30 degrees, specifically divided into three stages: 5 to 9 degrees, 10 to 25 degrees, and 26 to 30 degrees.

G5: Adjusting the video stream captured by the camera element 40 based on the azimuth angle change data and displaying it in the image display area 62 through the processor 11.

G6: Adjusting the video stream captured by the camera element 40 based on the rotation angle change data and displaying it in the image display area 62 through the processor 11.

G7: Determining whether |β-90| is less than or equal to a preset horizontal switching angle. If yes, executing G8. If no, executing G9.

G8: Adjusting the video stream captured by the camera element 40 based on the rotation angle change data and displaying it in the image display area 62 through the processor 11.

G9: Adjusting the video stream captured by the camera element 40 based on the azimuth angle change data and displaying it in the image display area 62 through the processor 11.

G10: Determining whether the angle between the preset axis of the attitude sensor 70 and the gravity direction is 0 degrees or within a preset range at the time point corresponding to the selected image 412 based on the azimuth angle change data. If yes, executing step G11. If no, executing step G12.

G11: Adjusting the image captured by the camera element 40 based on the rotation angle change data and displaying it in the image display area 62 through the processor 11.

G12: Adjusting the image captured by the camera element 40 based on the azimuth angle change data and displaying it in the image display area 62 through the processor 11.

In another preferred embodiment of the present invention, there is further provided an image processing method for an ear cleaning arrangement, comprising the following steps:

P1: identifying a target to be processed through acquiring a video stream captured by the camera element 40. The processor 11 receives the video stream captured by the camera element 40. The processor 11 selects one frame image from the video stream captured by the camera element 40 as a selected image 412. The processor 11 identifies the image of the ear spoon assembly 20 from the selected image 412. Furthermore, the processor 11 identifies the direction of the ear spoon assembly 20. The direction of the ear pick assembly refers to the target that the end of the ear spoon assembly 12 is facing. The selected image 412 is recorded as a recorded image 112. In a preferred embodiment of the present invention, the processor 11 draws an extension line along the ear spoon assembly, and the extension line can reach the target to be processed. The processor 11 may optionally display the extension line. The target to be processed is selected from an ear canal entrance or earwax. If the target to be processed is the ear canal entrance, then proceed to step T3; if the target to be processed is earwax, then proceed to step T4.

P2: acquiring the attitude information at the time point corresponding to the selected image 412 to obtain recorded attitude information 111, wherein the recorded attitude information comprises rotation angle change data and azimuth angle change data.

P3: during the process of the ear cleaning arrangement 100 moving toward the ear canal entrance, determining whether the ear canal entrance is still the target to be processed. Selecting the corresponding image processing method based on the movement mode of the ear cleaning arrangement 100. The processor 11 selects an image from the video stream acquired by the camera element 40 as a selected image 412. The processor 11 further acquires the direction of the ear spoon assembly 20 in the selected image 412. Theprocessor 11 determines whether the target to be processed has changed based on the direction of the ear spoon assembly 20. If the target to be processed has not changed, then proceed to step T4; if the target to be processed has changed, then proceed to step T1.

P4: Determining whether the ear cleaning arrangement 100 is shaking based on the attitude of the ear cleaning arrangement 100. If shaking occurs, adopting a corresponding image display method.

Wherein, step P4 further comprises the following steps:

P41: acquiring a segment of video stream, and selecting one frame image as a selected image 412.

P42: acquiring the current attitude information of the selected image 412 through the attitude sensor 70.

P43: comparing the recorded attitude information with the current attitude information to determine whether the ear cleaning arrangement 100 has changed its moving direction.

P44: If the ear cleaning arrangement 100 has not changed its moving direction, acquiring another current video stream.

P45: comparing the acquired video stream with the other current video stream to obtain video stream change characteristics.

P46: generating a preset image 43 for a preset time based on the video stream change characteristics.

P47: displaying the preset image in the image display area 62.

In another embodiment of the present invention, step P4 further comprises the following steps:

PA: acquiring a segment of video stream, and selecting one frame image as the selected image 412.

PB: acquiring the current attitude information of the selected image 412 through the attitude sensor 70, recording the current attitude information, and recording the selected image 412 as the recorded image 412.

PC: comparing the recorded attitude information with the current attitude information to determine whether the ear cleaning arrangement 100 has changed its moving direction.

PD: If the ear cleaning arrangement 100 has not changed its moving direction, displaying the recorded image in the image display area.

PE: Updating the recorded image 412 at a preset time.

In another embodiment of the present invention, step P4 employs the image processing method of the first operating mode or the second operating mode.

In another preferred embodiment of the present invention, an image processing method for an ear cleaning arrangement is provided, comprising the following steps:

T1: acquiring a video stream from within a user's ear canal. The user inserts the ear cleaning arrangement 100 into one of their ear canals to acquire the video stream from within the ear canal. Specifically, the ear spoon assembly 20 is inserted into one of the user's ear canals. The camera element 40 enters the user's ear canal along with the ear spoon assembly 20 to capture the video stream of the ear canal. The video stream of the ear canal captured by the camera element 40 is transmitted to the smart terminal 10. The acquired video stream of the ear canal is processed by the processor 11 and displayed on the display device 12.

T2: analyzing the acquired video stream to determine whether there is earwax in the ear canal video stream. If there is earwax in the ear canal video stream, the acquired video stream is further analyzed to obtain the direction of the ear spoon assembly 20. The earwax pointed to by the ear spoon assembly 20 is defined as the target to be cleaned. The current attitude information and current video stream information of the ear cleaning arrangement 100 are recorded. The current video stream information refers to the image information of the current frame recorded from the current video stream. The ear cleaning arrangement 100 further comprises an attitude sensor 70. In a preferred embodiment of the present invention, the attitude sensor 70 comprises a three-axis gyroscope 71 and a three-axis accelerometer 72. The three-axis gyroscope 71 is used to provide rotation angle change data to measure angular velocity and thereby determine the motion state of the object. The three-axis accelerometer 72 is used to provide direction change data to obtain acceleration information, thereby determining the movement direction and position of the object. Methods for obtaining movement direction, movement trajectory, and position through the three-axis gyroscope 71 and three-axis accelerometer 72 are well known in the art. A person skilled in the art should know how to obtain the current position, current attitude, movement direction, and movement trajectory of the ear cleaning arrangement through the three-axis gyroscope 71 and three-axis accelerometer 72.

T3: monitoring the movement trajectory and movement direction of the ear cleaning arrangement 100 by respectively acquiring the attitude information provided by the attitude sensor 70 and the video stream information provided by the camera element 40.

T4: determining a new target to be cleaned based on the direction of the ear spoon assembly.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An image processing method for an ear cleaning arrangement is executed on one or more processors for processing image information collected by an ear cleaning arrangement, wherein the ear cleaning arrangement comprises a cleaning assembly, a fixing assembly, a camera element, an attitude sensor, and a light source assembly, wherein the camera element and the light source assembly are mounted on the fixing assembly, and the cleaning assembly is disposed at one end of the fixing assembly, wherein at least part of the cleaning assembly is within the image capture range of the camera element, wherein the method comprises the steps of:
   S1. determining a video stream display area on an operation interface, wherein the video stream display area is circular, and the video stream in the video stream display area is sourced from the camera element;
   S2. defining a background area on the operation interface, wherein the background area surrounds the video stream display area, and setting the background area to a uniform background color:
   S3. acquiring a current display mode and processing the video stream collected by the camera element according to the corresponding display mode to obtain a processed video stream; and
   S4. displaying the processed video stream in the video stream display area;
   wherein the uniform background color is black;
   wherein the step S3 further comprises the following steps:
   S31. identifying the cleaning assembly and a video background in the video stream collected by the camera element respectively;
   S32. determining the current display mode, wherein if the current display mode is a horizontal mode, executing step S33, and if the current display mode is a dynamic mode, executing step S34;
   S33. when the ear cleaning arrangement rotates around a central axis of the ear cleaning arrangement, fixing the video background, and the cleaning assembly rotates with the ear cleaning arrangement; and
   S34. when the ear cleaning arrangement rotates around the central axis of the ear cleaning arrangement, fixing the cleaning assembly at a position in the video stream display area, and the video background rotates with the ear cleaning arrangement;
   wherein the step S33 further comprises the following steps:
   S331. separating the cleaning assembly image and the video background to obtain a cleaning assembly layer and a video background layer;
   S332. locking the video background layer so that the video background layer is fixed in the video stream display area;
   S333. removing the cleaning assembly layer;
   S334. removing the video background of the video stream collected by the camera element to obtain the cleaning assembly layer of the video stream collected by the camera element; and
   S335. displaying the locked video background layer and the cleaning assembly layer of the video stream collected by the camera element in the video stream display area of the operation interface.

2. An image processing method for an ear cleaning arrangement is executed on one or more processors for processing image information collected by an ear cleaning arrangement, wherein the ear cleaning arrangement comprises a cleaning assembly, a fixing assembly, a camera element, an attitude sensor, and a light source assembly, wherein the camera element and the light source assembly are mounted on the fixing assembly, and the cleaning assembly is disposed at one end of the fixing assembly, wherein at least part of the cleaning assembly is within the image capture range of the camera element, wherein the method comprises the steps of:
   S1. determining a video stream display area on an operation interface, wherein the video stream display area is circular, and the video stream in the video stream display area is sourced from the camera element;

S2. defining a background area on the operation interface, wherein the background area surrounds the video stream display area, and setting the background area to a uniform background color:

S3. acquiring a current display mode and processing the video stream collected by the camera element according to the corresponding display mode to obtain a processed video stream; and S4. displaying the processed video stream in the video stream display area;

wherein the uniform background color is black;

wherein the step S3 further comprises the following steps:

S31. identifying the cleaning assembly and a video background in the video stream collected by the camera element respectively;

S32. determining the current display mode, wherein if the current display mode is a horizontal mode, executing step S33, and if the current display mode is a dynamic mode, executing step S34;

S33. when the ear cleaning arrangement rotates around a central axis of the ear cleaning arrangement, fixing the video background, and the cleaning assembly rotates with the ear cleaning arrangement; and S34. when the ear cleaning arrangement rotates around the central axis of the ear cleaning arrangement, fixing the cleaning assembly at a position in the video stream display area, and the video background rotates with the ear cleaning arrangement;

wherein the step S34 further comprises the following steps:

S341. separating the cleaning assembly image and the video background to obtain a cleaning assembly layer and a video background layer;

S342. locking the cleaning assembly layer so that the cleaning assembly layer is fixed at a position in the video stream display area;

S343. removing the video background layer;

S344. removing the cleaning assembly of the video stream collected by the camera element to obtain the video background layer of the video stream collected by the camera element; and S335. displaying the locked cleaning assembly layer and the video background layer of the video stream collected by the camera element in the video stream display area of the operation interface, wherein the video background layer collected by the camera element is placed under the locked cleaning assembly layer.

* * * * *